United States Patent
Abrams et al.

(10) Patent No.: US 10,426,351 B2
(45) Date of Patent: Oct. 1, 2019

(54) SYSTEMS AND METHODS FOR SPATIAL POSITIONING OF DIAGNOSTIC AND OR TREATMENT PROBE BASED ON SURFACE PROFILE DETECTION

(71) Applicant: QUANTUM DENTAL TECHNOLOGIES INC., Toronto, ON (CA)

(72) Inventors: Stephen Abrams, Toronto (CA); Josh Silvertown, Toronto (CA); Koneswaran S. Sivagurunathan, Toronto (CA)

(73) Assignee: QUANTUM DENTAL TECHNOLOGIES INC., Toronto, On (CA)

( * ) Notice: Subject to any disclaimer, the term of this patent is extended or adjusted under 35 U.S.C. 154(b) by 0 days.

(21) Appl. No.: 15/775,126

(22) PCT Filed: Nov. 10, 2016

(86) PCT No.: PCT/CA2016/051307
§ 371 (c)(1),
(2) Date: May 10, 2018

(87) PCT Pub. No.: WO2017/079837
PCT Pub. Date: May 18, 2017

(65) Prior Publication Data
US 2018/0368694 A1    Dec. 27, 2018

Related U.S. Application Data

(60) Provisional application No. 62/253,303, filed on Nov. 10, 2015.

(51) Int. Cl.
*A61B 1/24* (2006.01)
*A61B 5/00* (2006.01)
(Continued)

(52) U.S. Cl.
CPC .......... *A61B 5/0088* (2013.01); *A61B 1/045* (2013.01); *A61B 1/24* (2013.01); *A61B 5/0071* (2013.01);
(Continued)

(58) Field of Classification Search
CPC ......... A61B 5/0088; A61B 1/045; A61B 1/24; A61B 5/0071; A61B 5/0075;
(Continued)

(56) References Cited

U.S. PATENT DOCUMENTS 6,584,341 B1   6/2003   Mandelis et al.
8,306,608 B2   11/2012  Mandelis et al.
(Continued)

FOREIGN PATENT DOCUMENTS

WO    2014/125037 A1    8/2014

OTHER PUBLICATIONS

International Search Report PCT/CA201/051307, dated May 18, 2017,3 Pages.

*Primary Examiner* — Roy M Punnoose
(74) *Attorney, Agent, or Firm* — Hilll & Schumacher

(57) ABSTRACT

Systems and methods are disclosed in which a diagnostic probe is configured for performing diagnostic measurements and/or therapeutic interventions and for measuring the local surface profile of a local surface region an object. Various example embodiments are described in which the surface profile of the local surface region, when compared to the surface profile of an extended surface region, is employed to provide guidance for positioning and/or orienting the probe when performing a diagnostic measurement. The surface profile within the local surface region may be employed to generate feedback for repeating a previous diagnostic measurement, such that the repeat measurement is performed at the previous location on the object. In other embodiments, (Continued)

surface profile detection is employed to control the positional and/or orientational probe alignment during an iterative tissue removal method in which successive tissue layers are removed when the presence of a pathology is confirmed via a diagnostic measurement.

24 Claims, 17 Drawing Sheets

(51) Int. Cl.
*A61C 19/04* (2006.01)
*A61B 5/107* (2006.01)
*A61B 1/045* (2006.01)
*A61B 8/08* (2006.01)
*A61C 1/00* (2006.01)
*A61C 9/00* (2006.01)
*A61N 5/06* (2006.01)

(52) U.S. Cl.
CPC .......... *A61B 5/0075* (2013.01); *A61B 5/0077* (2013.01); *A61B 5/1077* (2013.01); *A61B 5/4836* (2013.01); *A61B 5/743* (2013.01); *A61B 8/0875* (2013.01); *A61C 1/0007* (2013.01); *A61C 1/0046* (2013.01); *A61C 9/006* (2013.01); *A61C 9/0086* (2013.01); *A61C 19/04* (2013.01); *A61N 5/0616* (2013.01)

(58) Field of Classification Search
CPC ... A61B 5/0077; A61B 5/1077; A61B 8/0875; A61B 5/743; A61B 5/4836; A61C 19/04; A61C 9/0086; A61C 9/006; A61C 1/0046; A61C 1/0007
USPC ........................................................ 356/603
See application file for complete search history.

(56) References Cited

U.S. PATENT DOCUMENTS

| | | |
|---|---|---|
| 8,878,905 B2 | 11/2014 | Fisker et al. |
| 9,442,069 B2 | 9/2016 | Jeon et al. |
| 9,506,808 B2 | 11/2016 | Jeon et al. |
| 2013/0330686 A1* | 12/2013 | Kaji ..................... A61B 5/0088 433/30 |
| 2014/0186794 A1 | 7/2014 | Deichmann et al. |
| 2014/0212832 A1 | 7/2014 | Fisker et al. |
| 2015/0018613 A1 | 1/2015 | Hollenbeck et al. |
| 2015/0164335 A1 | 6/2015 | Van Der Poel et al. |

* cited by examiner

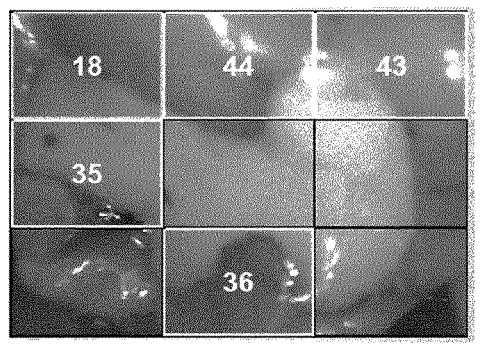 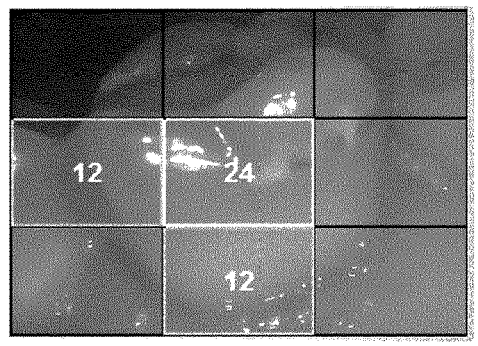
FIG. 1B                    FIG. 1C

Photographic image of scanned area (Spot A)

PLM image of Spot A

| Spot | Canary Number | DIAGNOdent reading | PLM Lesion Depth (µ) |
|------|---------------|--------------------|-----------------------|
| A    | 55 ± 5        | 0 ± 0              | 548.34                |

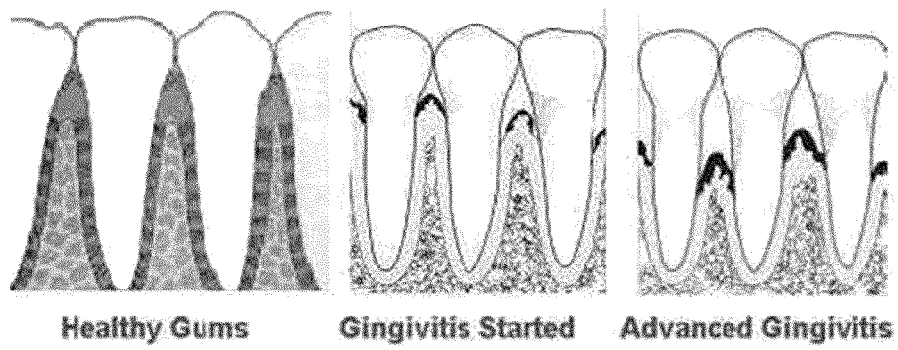
Healthy Gums    Gingivitis Started    Advanced Gingivitis
FIG. 13A          FIG. 13B              FIG. 13C
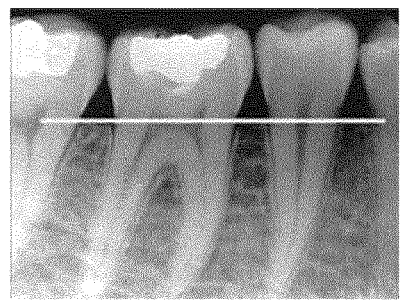 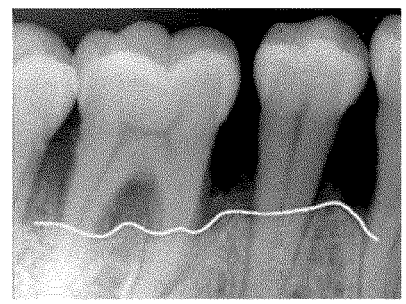
FIG. 13D                FIG. 13E

SYSTEMS AND METHODS FOR SPATIAL POSITIONING OF DIAGNOSTIC AND OR TREATMENT PROBE BASED ON SURFACE PROFILE DETECTION

CROSS-REFERENCE TO RELATED APPLICATION

This application is a National Phase application claiming the benefit of the international PCT Patent Application No. PCT/CA2016/051307, filed on Nov. 10, 2016, in English, which claims priority to U.S. Provisional Application No. 62/253,303, titled "SYSTEMS AND METHODS FOR SPATIAL POSITIONING OF DIAGNOSTIC PROBE BASED ON SURFACE PROFILE DETECTION" and filed on Nov. 10, 2015, the entire contents of which are incorporated herein by reference.

BACKGROUND

The present disclosure relates to probe-based diagnostic measurement devices. More particularly, the present disclosure relates to intraoral detection probes.

SUMMARY

Systems and methods are disclosed in which a diagnostic probe is configured for performing diagnostic measurements and/or therapeutic interventions and for measuring the local surface profile of a local surface region an object. Various example embodiments are described in which the surface profile of the local surface region, when compared to the surface profile of an extended surface region, is employed to provide guidance for positioning and/or orienting the probe when performing a diagnostic measurement. The surface profile within the local surface region may be employed to generate feedback for repeating a previous diagnostic measurement, such that the repeat measurement is performed at the previous location on the object. In other embodiments, surface profile detection is employed to control the positional and/or orientational probe alignment during an iterative tissue removal method in which successive tissue layers are removed when the presence of a pathology is confirmed via a diagnostic measurement.

Accordingly, in a first aspect, there is provided system for performing a probe-based diagnostic measurement, the system comprising:
a probe comprising:
an optical surface profile detection subsystem configured to direct optical energy onto a local surface region of an object and to detect, from the local surface region, scattered optical energy suitable for generating a surface profile of the local surface region; and
a diagnostic subsystem aligned relative to said optical surface profile detection subsystem, wherein said diagnostic subsystem is configured to interrogate the local surface region and/or a subsurface region beneath the local surface region; and
control and processing hardware operatively coupled to said optical surface profile detection subsystem and said diagnostic subsystem;
wherein said control and processing hardware is configured to perform the following operations to provide guidance for positioning said probe to repeat a previous diagnostic measurement, wherein the previous diagnostic measurement was performed at a previous local surface region:
a) controlling said optical surface profile detection subsystem to interrogate a current local surface region that is currently within a field of view of said optical surface profile detection subsystem, and obtaining signals from said optical surface profile detection subsystem that are generated in response to detection of the scattered optical energy;
b) processing the signals and generating local surface profile data characterizing a three-dimensional surface profile of the current local surface region;
c) processing the local surface profile data and previously-measured surface profile data to locate the current local surface region within the three-dimensional surface profile of the object, the previously-measured surface profile data characterizing a three-dimensional surface profile of at least a portion of the object;
d) providing feedback for moving said probe such that the current local surface region is moved toward the previous local surface region;
e) repeating steps a) to d) until the current local surface region is aligned, within a pre-selected spatial alignment range, with the previous local surface region; and
f) providing output suitable to initiate the repeating of the diagnostic measurement.

In another aspect, there is provided a system for performing a probe-based diagnostic measurement, the system comprising:
a probe comprising:
an optical surface profile detection subsystem configured to direct optical energy onto a local surface region of an object and to detect, from the local surface region, scattered optical energy suitable for generating a surface profile of the local surface region; and
a diagnostic subsystem aligned relative to said optical surface profile detection subsystem, wherein said diagnostic subsystem is configured to interrogate the local surface region and/or a subsurface region beneath the local surface region; and
control and processing hardware operatively coupled to said optical surface profile detection subsystem and said diagnostic subsystem;
wherein said control and processing hardware is configured to perform the following operations to provide guidance for positioning said probe for performing a diagnostic measurement within a pre-selected local surface region:
a) controlling said optical surface profile detection subsystem to interrogate a current local surface region that is currently within a field of view of said optical surface profile detection subsystem, and obtaining signals from said optical surface profile detection subsystem that are generated in response to detection of the scattered optical energy;
b) processing the signals and generating local surface profile data characterizing a three-dimensional surface profile of the current local surface region;
c) processing the local surface profile data and previously-measured surface profile data to locate the current local surface region within the three-dimensional surface profile of the object, the previously-measured surface profile data characterizing a three-dimensional surface profile of at least a portion of the object;

d) providing feedback for moving said probe such that the current local surface region is moved toward the pre-selected local surface region;

e) repeating steps a) to d) until the current local surface region is aligned, within a pre-selected spatial alignment range, with the pre-selected local surface region; and f) providing output suitable for initiating the diagnostic measurement.

In another aspect, there is provided a system for performing a probe-based diagnostic measurement, the system comprising:

a probe comprising:

an optical surface profile detection subsystem configured to direct optical energy onto a local surface region of an object and to detect, from the local surface region, scattered optical energy suitable for generating a surface profile of the local surface region; and a diagnostic subsystem aligned relative to said optical surface profile detection subsystem, wherein said diagnostic subsystem is configured to interrogate the local surface region and/or a subsurface region beneath the local surface region; and control and processing hardware operatively coupled to said optical surface profile detection subsystem and said diagnostic subsystem;

wherein said control and processing hardware is configured to perform the following operations in association with a diagnostic measurement made at the local surface region:

a) controlling said optical surface profile detection subsystem to interrogate the local surface region positioned within the field of view of said probe, and obtaining signals from said optical surface profile detection subsystem that are generated in response to detection of the scattered optical energy;

b) processing the signals and generating local surface profile data characterizing a three-dimensional surface profile of the local surface region;

c) processing the local surface profile data and previously-measured surface profile data to locate the local surface region within the three-dimensional surface profile of the object, the previously-measured surface profile data characterizing a three-dimensional surface profile of at least a portion of the object; and d) generating an image of the three-dimensional profile of at least a portion of the object, the image comprising a graphical annotation associated with the diagnostic measurement, wherein the graphical annotation provides an indication of the location corresponding to the diagnostic measurement.

In another aspect, there is provided a method of repeating a previous diagnostic measurement with the system as described above, the method comprising:

identifying the previous diagnostic measurement on a user interface operably interfaced with the system, and wherein the previous diagnostic measurement has associated therewith the previous local surface region;

positioning the probe such that the field of view of the probe overlaps with a portion of the object to be re-measured;

controlling the probe to interrogate the surface profile of the current local surface region;

receiving the feedback from the system for moving the probe such that the current local surface region currently positioned within the field of view of the probe is moved toward the previous local surface region;

moving the probe according the feedback until output is received indicating that the current local surface region sufficiently corresponds to the previous local surface region; and controlling the system to repeat the diagnostic measurement.

In another aspect, there is provided a method of controlling a diagnostic and therapeutic probe, the diagnostic and therapeutic probe comprising:

an optical surface profile detection subsystem configured to direct optical energy onto a local surface region of an object and to detect, from the local surface region, scattered optical energy suitable for generating a surface profile of the local surface region;

a diagnostic subsystem aligned relative to the optical surface profile detection subsystem, wherein the diagnostic subsystem is configured to interrogate the local surface region and/or a subsurface region beneath the local surface region; and a therapeutic subsystem aligned relative to the optical surface profile detection subsystem, wherein the therapeutic subsystem is configured for local tissue removal;

the method comprising:

a) employing the diagnostic and therapeutic probe to identify an initial surface region associated with a surface or subsurface pathology;

b) employing the optical surface profile detection subsystem to interrogate the initial surface region, and obtaining signals from the optical surface profile detection subsystem that are generated in response to detection of optical energy scattered from the initial surface region;

c) processing the signals and generating initial local surface profile data characterizing a three-dimensional surface profile of the initial surface region;

d) sending control signals to the therapeutic subsystem to initiate removal of a first tissue layer;

e) performing an additional diagnostic measurement with the diagnostic subsystem to determine whether or the pathology is still present;

f) in the event that the presence of the pathology is detected, sending control signals to the therapeutic subsystem to initiate removal of an additional layer of tissue; and g) repeating steps e) and f) until the pathology is no longer detected;

wherein prior to performing one or both of steps e) and f), the following steps are performed to ensure correct positional and/or orientational alignment of the diagnostic and therapeutic probe:

employing the optical surface profile detection subsystem to interrogate a current local surface region that is currently within a field of view of the optical surface profile detection subsystem, and obtaining additional signals from the optical surface profile detection subsystem that are generated in response to detection of optical energy scattered from the current local surface region;

processing the additional signals and generating current local surface profile data characterizing a three-dimensional surface profile of the current local surface region;

processing the initial local surface profile data and the current local surface profile data to identify a positional and/or orientational misalignment of the diagnostic and therapeutic probe relative to an initial position and orientation of the diagnostic and therapeutic probe when the local surface region was identified in step a); and in the event of detection of the positional and/or orientational misalignment of the diagnostic and therapeutic probe, preventing further diagnostic measurements or tissue removal steps until the positional and/or orientational misalignment is corrected.

In another aspect, there is provided a method of measuring alveolar bone height using a diagnostic probe, the diagnostic probe comprising:

an optical surface profile detection subsystem; and an infrared detection subsystem aligned relative to the optical surface profile detection subsystem, wherein the infrared detection subsystem is configured direct infrared light onto a tissue surface and detect scattered infrared light from tissue regions below the tissue surface;

the method comprising:

while moving the diagnostic probe relative at least a portion of the maxialla and mandible;

employing the optical surface profile detection subsystem to direct optical energy onto a plurality of tooth and gum surfaces, and to detect, spatial profile signals associated with scattered optical energy;

employing the infrared detection subsystem to direct infrared light onto the gum surfaces, and detecting infrared signals associated with scattered infrared light that is scattered from regions below the gum surfaces;

processing the spatial profile signals to determine a three-dimensional surface profile associated with the plurality of tooth and gum surfaces;

processing the infrared signals and the surface profile to identify alveolar bone regions within the surface profile that are associated with the presence of alveolar bone beneath the tissue surface.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1B and 1C show example images of teeth having a grid overlaid thereupon, with photothermal detection measurement values shown in various portions of the grid.

FIGS. 13A-C illustrate the changes of the bone level during the progression of gingivitis and or periodontal disease.

FIGS. 13D-E show (A) an x-ray image of teeth in a subject with a high bone level and the absence of gingivitis and or periodontal disease, and (B) an x-ray image of teeth in a subject with a low bone level and the presence of gingivitis and or periodontal disease.

DETAILED DESCRIPTION

Figure 1A:
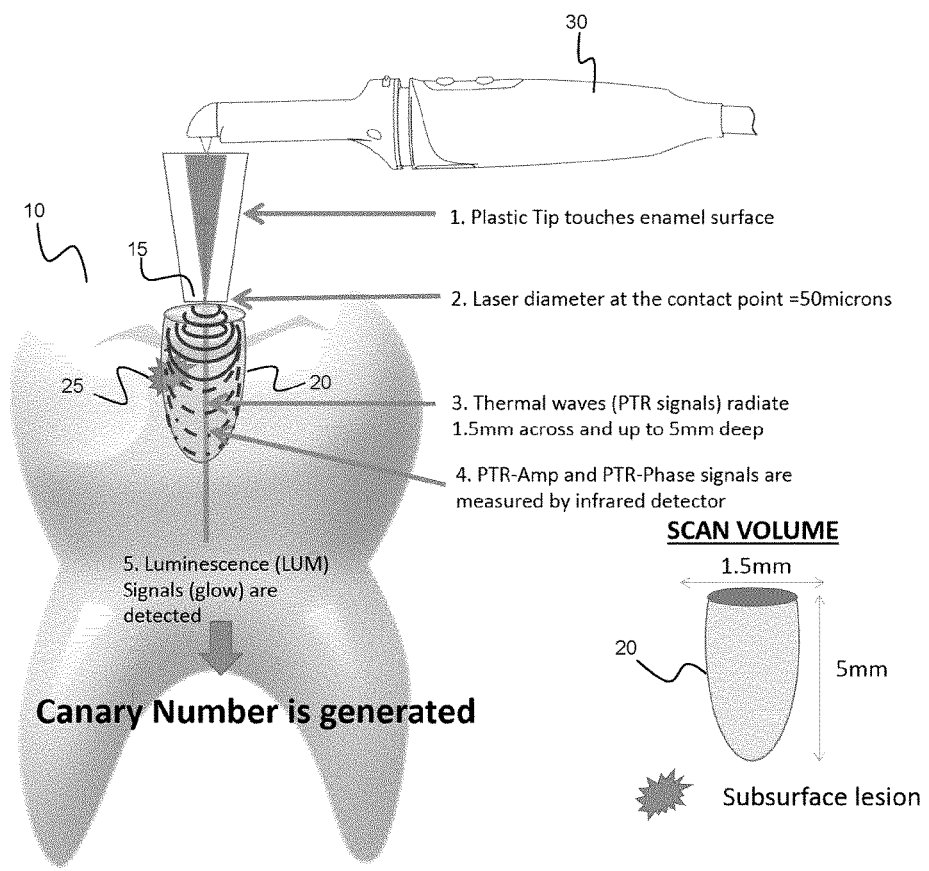
FIG. 1A illustrates an example embodiment of a diagnostic detection modality involving the photothermal detection of subsurface lesions in teeth.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure provide systems and methods in which a diagnostic measurement subsystem and a surface profile detection system are integrated into a diagnostic detection probe. As will be described in detail below, the integration of surface profile detection with diagnostic measurement in a diagnostic probe enables the use of surface profile detection to determine the position and/or orientation of the diagnostic probe, and to use this probe position and/or orientation in order to provide guidance for performing diagnostic measurements.

In several example embodiments, the surface profile of a local surface region of an object that is scanned by the integrated probe is compared to previously-obtained surface profile data characterizing the object (or at least a portion of the object) in order to locate the local surface region within an extended surface region of an object. As will be explained below, the local surface region may be located by spatial registration of the local surface profile data to the previously-obtained surface profile data.

In some example embodiments described below, the ability to locate the local surface region interrogated by the probe may be employed to provide feedback for guiding the probe into a particular position and/or orientation for making a diagnostic measurement. For example, the feedback may be provided to repeat a previous diagnostic measurement with the probe in the same, or approximately the same, position and/or orienting. In another example embodiment, feedback may be provided to move the probe such that it is positioned in a pre-selected position and/or orientation for making a diagnostic measurement.

The ability to locate the local surface region within the surface profile of the object may be employed, for example, to determine and record the location, on the object, at which a diagnostic measurement was made. This location information may then be employed, for example, to annotate a three-dimensional image of the object with information identifying the location of the diagnostic measurement.

FIG. 1A illustrates an example diagnostic modality employing photothermal detection, as applied to the detection of subsurface defects in teeth. An intraoral probe 30 is employed to generate a beam of excitation optical energy that is directed onto the surface of tooth 10, forming spot 15. The absorbed optical energy responsively produces photothermal waves, which probe a region 20 including both the surface region and the subsurface region. As shown in the figure, a subsurface lesion 25 generates a perturbation to the photothermal signal that is detected by the probe. Examples of photothermal-based probe systems are described in Patent Cooperation Treaty Application No. PCT/CA2011/50303, titled "HANDPIECE WITH INTEGRATED OPTICAL SYSTEM FOR PHOTOTHERMAL RADIOMETRY AND LUMINESCENCE MEASUREMENTS", and filed on May 13, 2011, which is incorporated herein by reference in its entirety.

As shown in FIG. 1A, the intraoral probe directs the excitation beam onto a small spot on the tooth surface. During clinical practice, it may be important or beneficial to scan a specific location on the tooth surface. For example, as shown in FIGS. 1B and 10, the measurements may be made according to a grid that divides the tooth surface into a set of different spatial regions. The diagnostic measurements from the regions may then be obtained and displayed on an image of the tooth surface, as shown in the figures.

Unfortunately, such an approach can be difficult or problematic for a user or operator, due to the need for the user to carefully position the probe relative to the tooth surface in order to scan a given subregion. In some cases, the user may incorrectly scan the wrong location, resulting in an erroneous reading. In other cases, it may be desirable for a user to repeat a diagnostic measurement of a previously measured location on the tooth surface, and it may be very difficult to properly position the probe in order to ensure that the same region is re-measured.

These problems may be overcome by various embodiments of the present disclosure in which an integrated probe is provided that employs surface profile scanning to guide the positioning of the probe, such that feedback is provided to assist in the positioning of the probe relative to the object being scanned.

Figure 2A:
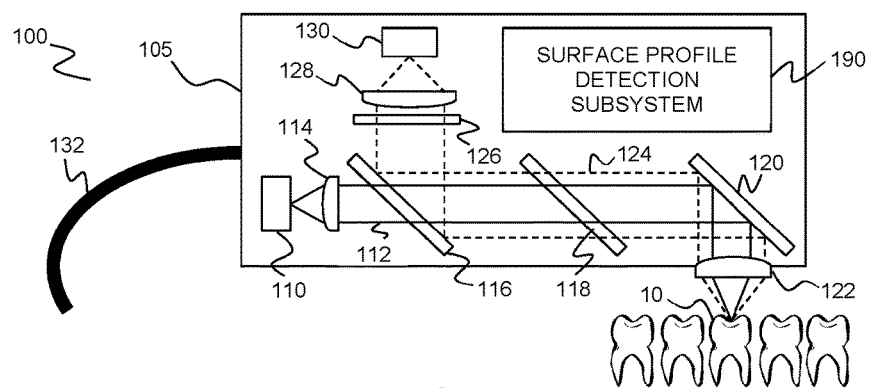
FIGS. 2A-2D illustrate several example embodiments of an integrated diagnostic probe having a diagnostic measurement subsystem and a surface prolife detection subsystem.
Figure 2B:
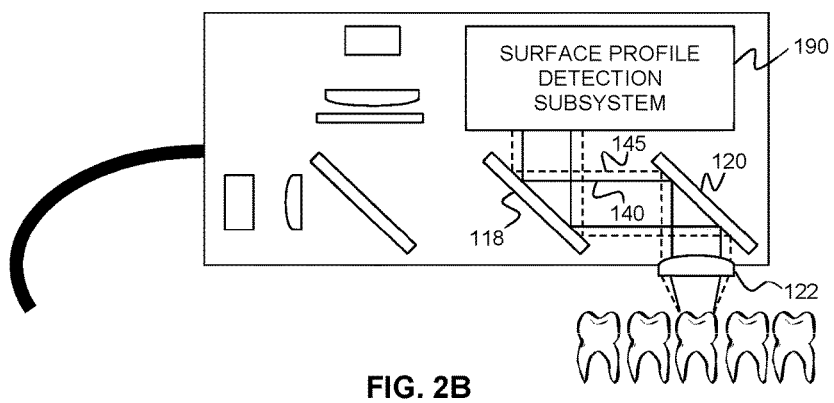

Referring now to FIGS. 2A and 2B, an example embodiment of an integrated probe 100 is illustrated where the detection modality is optical. The example integrated probe 100 includes a housing 105, which houses a diagnostic detection subsystem and a surface profile scanning subsystem 190. The diagnostic detection subsystem, in the present example embodiment, includes an optical source 110 which generates excitation optical beam 112 (an excitation energy beam) that is collimated by lens 114, passes through a first dichroic mirror 116 and a second dichroic mirror 118, before being deflected by a mirror 120 and focused onto the tooth 10 by a lens 122. The excitation optical beam 112 is absorbed by the tooth 10 and responsively generates optical signals at the tooth surface and/or beneath the tooth surface, which are collected by the lens 122 to form collected optical beam 124, which is directed within the housing 105 by the mirror 120. The first dichroic mirror 116 deflects at least a portion of the collected optical beam (e.g. rejecting scattered excitation energy), which is then optionally spectrally filtered by optical filter 126 (e.g. a high-pass filter), and focused by a lens 128 onto a detector 130. In the example embodiment shown in FIG. 2A, control signals (for controlling the optical source 110) and received signals from the detector 130 are transmitted through cable 132 to a control and processing unit (described further below). Alternatively, the control signals and/or detected signals may be transmitted wirelessly. In another example implementations, processing electronics may be included within the housing 105 for partial or complete processing of control signals and/or received signals.

The example embodiment shown in FIGS. 2A and 2B may be implemented according to a number of different optical modalities, including, but not limited to, luminescence detection, fluorescence detection, and photothermal detection. For example, in one implementation, the optical components of the diagnostic detection system may be configured for photothermal detection as per the example embodiments described and illustrated in Patent Cooperation Treaty Application No. PCT/CA2011/50303. In another example implementation, the optical components of the diagnostic detection system may be configured for themophotonic dynamic imaging, as per the example embodiments described and illustrated in Patent Cooperation Treaty Application No. PCT/CA2012/050035, titled "SYSTEMS AND METHODS FOR THERMOPHOTONIC DYNAMIC IMAGING", and filed on Jan. 20, 2012, which is incorporated herein by reference in its entirety.

It will be understood that the example embodiment shown in FIGS. 2A and 2B is merely provided as illustrative example, and is not intended to limit the scope of the present disclosure to systems and methods for performing optical diagnostic measurements on teeth. The specific application of the detection of optical (e.g. photothermal) signals from teeth is provided as a non-limiting example, and other probe configurations, and applications, may be employed without departing from the intended scope of the present disclosure. For example, the diagnostic detection subsystem may employ a non-optical detection modality, such as ultrasound detection. Various non-limiting examples of diagnostic modalities include photothermal detection, combined photothermal and luminescence detection, photothermal imaging, combined photothermal and luminescence imaging, infrared imaging, thermal imaging, optical coherence tomography, ultrasound detection, ultrasound imaging, and x-ray imaging.

Figure 12A:
FIGS. 12A-C show (A) an image showing the presence of erosion, (B) an image of a tooth showing the presence of a white spot, and (C) a polarized light microscopy image of a lesion beneath a white spot.

Moreover, as described above, the diagnostic detection system may employ a detection modality that provides detection of surface features and/or subsurface features. For example, in the field of dentistry, surface changes may involve one or more of the following issues or disease processes:

Erosion of the surface or loss of surface tissue due to exposure to acidic drinks. Gastric reflux, abrasive action of tooth brushing and/or clenching and or grinding: The photograph shown in FIG. 12A shows erosion that is spread across the entire dentition. The erosion initially appears as minor colour changes (area in the circle) but becomes more advanced as the enamel surface is removed. Erosion or loss of surface tissue could be measured, for example, by comparing the changes in surface topography over time (e.g. obtaining initial surface profile data when the probe is positioned and optionally aligned at an initial local surface region, and obtaining subsequent surface profile data when the probe is repositioned and optionally realigned at with the initial local surface region at a later point in time, and comparing the initial surface profile data with the subsequent surface profile data to detect differences in surface profile that are associated with erosion, and/or abrasion/abfraction, as described below), changes in surface and subsurface colouration over time, and/or measuring the height of various sections of the tooth surface or the entire tooth and then comparing it to measurements taken over time. Erosion can affect the entire tooth surface or small sections of the tooth surface. At times, the cusp tips of the teeth may become "cup shaped" as they are subjected to erosion. At times the surface enamel may be worn away allowing the underlying dentin, which has a very strong yellow colour to shine through the enamel or it may become exposed to the surface.

Staining: This would involve measuring and comparing changes in surface colour due to the accumulation of surface or near surface stain. One would use this when monitoring colour change during bleaching or whitening procedures. There would be need to go back and examine the entire tooth surface and compare it to previous data in order to see if there had been any colour change. This is currently done using visual examination since photographs have a large amount of reflection.

Abrasion and or abfraction which involves mechanical loss of the tooth surface by exposure to heavy biting forces, excessive forces applied to the tooth surface with a tooth brush or other mechanical devices and other types of forces or habits that would cause the loss of tooth structure. The changes on the tooth surface due to abrasion or abfraction are very similar to the changes one would find with erosion (as outlined above). Such changes could be measured by comparing the changes in surface topography over time, changes in surface and sub surface colouration over time and or measuring the height of various sections of the tooth surface or the entire tooth and then comparing it to measurements taken over time. Abrasion and/or abfraction can affect the entire tooth surface or small sections of the tooth surface. At times the surface enamel may be worn away allowing the underlying dentin, which has a very strong yellow colour to shine through the enamel or it may become exposed to the surface.

Wear on the margins of restorations or fillings: As restorations or fillings age the edges or margins begin to open and they are no as well adapted to the adjacent tooth surface. Initially, using an intra-oral camera, one sees a small gap between the filling and the tooth surface and over time this will stain leaving a small brown line in the area. At times, the surrounding tooth structure would wear away due to erosion, abrasion or abfraction (as mentioned above) leaving the restoration position slightly above the tooth surface and not having its edges or margins flush with the tooth surface.

Figure 12B:
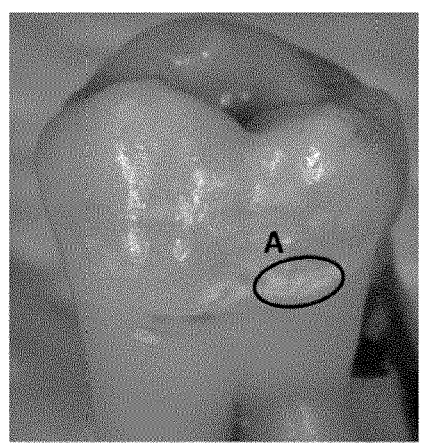
Figure 12C:
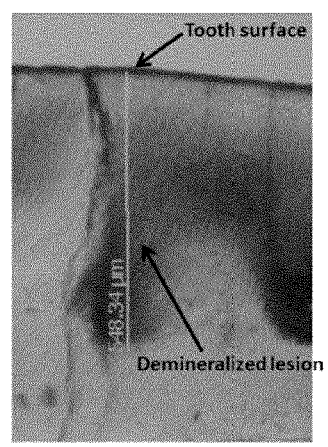

White spots: These are early indications of the start of tooth decay or caries at or beneath the tooth surface. A suitable diagnostic probe, such as one that employs photothermal and luminescence detection, can measure these areas, the measurement may require or benefit from controlled probe positioning and angulation/orientation in order to accurately measure the changes beneath the surface. The detection of white spots using visible spectrum optical imaging and polarized light microscopy is shown in FIGS. 12B and 12C, respectively.

Non-limiting examples of detection modalities that may be employed for surface detection include colorimetric detection, surface profilometry, and luminescence detection.

In another example, subsurface changes may involve one or more of the following issues or disease processes:

Caries or tooth decay;
Caries or tooth decay beneath the intact margins of a filling or crown;
Caries or tooth decay beneath a surface sealant;
Cracks around the edges of fillings; and
Cracks at the base of fillings.

Non-limiting examples of detection modalities that may be employed for subsurface detection include photothermal detection, optical coherence tomography, and ultrasound, x-rays, cone beam CT scanning, transillumination with various wavelengths of light.

FIG. 2B schematically shows an example implementation of a portion of the optical circuit employed for routing optical energy to and from the surface profile detection subsystem 190. As shown schematically in the figure, optical energy is directed (e.g. focused, scanned, projected) onto the tooth surface, as shown by beam 140, and scattered optical energy is collected and detected, as shown by collected beam 145. The surface profile detection subsystem 190 may employ any suitable surface profile detection modality. Non-limiting example modalities include confocal microscopy, optical coherence tomography, structured light, triangulation, stereoscopy, interferometry, and variations thereof. In one example implementation, the surface profile detection subsystem includes a light source for generating and projecting one or more structured light patterns on the object, and a camera for detecting the perturbations to the light patterns due to the changes in surface profile. In another example implementation, the surface profile detection subsystem includes a confocal optical system, including a light source, a confocal optical scanning and imaging assembly, and a detector.

In the example embodiment shown, the surface profile detection subsystem 190 shares a portion of its optical path with the diagnostic subsystem, such that both subsystems include at least one common optical component. In an alternative example embodiment, the surface profile detection subsystem 190 can be provided as an independent subsystem that does not share components with the diagnostic detection subsystem. For example, this would be the case when the detection modality of the diagnostic subsystem is not optical (e.g. the detection modality is ultrasound).

Figure 2C:
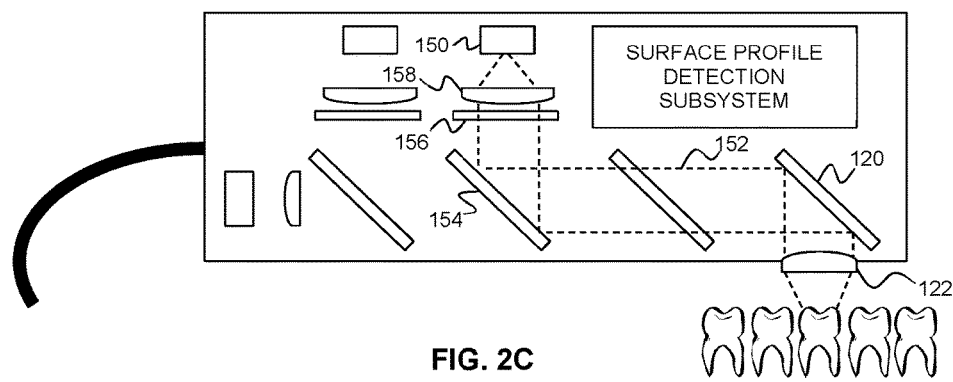

In another example embodiment, illustrated in FIG. 2C, the diagnostic detection subsystem may also include a camera 150, such as a colour camera, which may be a high-definition video camera (e.g. having 1080p or 4K resolution, or greater resolution). Light scattered or emitted from the tooth is collected by lens 122, reflected by mirror 120 to form beam 152, partially reflected by a beamsplitter 154, optionally filtered by filter a 156, and focused by a lens 158 onto the camera 150. In one example implementation, the camera 150 is an infrared camera.

Figure 2D:
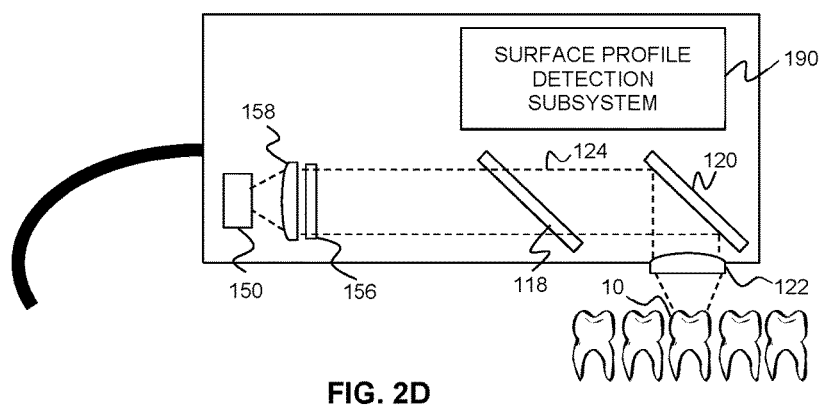

FIG. 2D illustrates another example embodiment in which the diagnostic detection system includes a camera, such as a colour (e.g. high-definition) camera or an infrared camera 150. Light scattered or emitted from the tooth is collected by lens 122, reflected by mirror 120 to form beam 152, optionally filtered by filter a 156, and focused by a lens 158 onto the camera 150. In one example implementation, both a colour camera and an infrared camera may be provided in the housing, in which case a beamsplitter would be included to direct a portion of the collected light to a second camera.

In FIGS. 2A and 2B, the diagnostic detection subsystem is shown as being configured for performing a diagnostic measurement at a point, or a focused spot. However, in other implementations, the diagnostic detection subsystem may include an imaging camera and imaging optics for performing a spatially-resolved diagnostic measurement over an extended area.

Figure 3A:
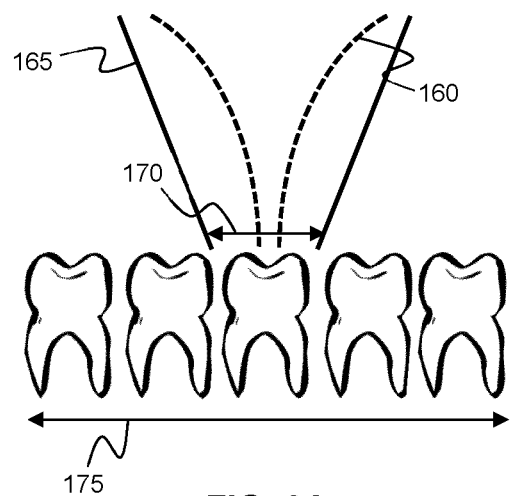
FIGS. 3A and 3B illustrate the repositioning of an integrated probe according to guidance based on surface profile detection.
Figure 3B:
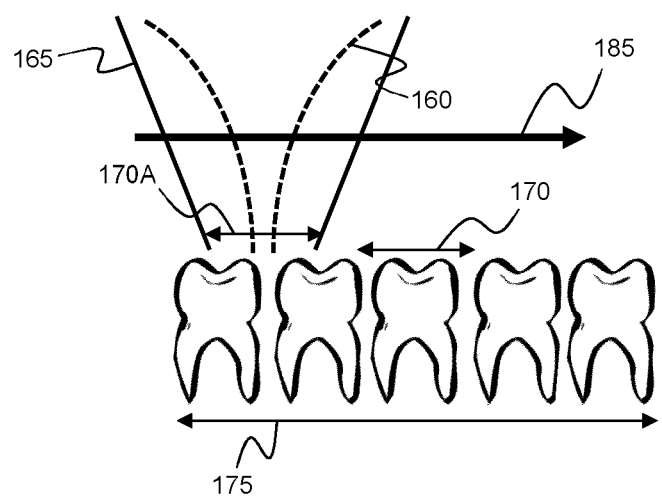
Figure 4A:
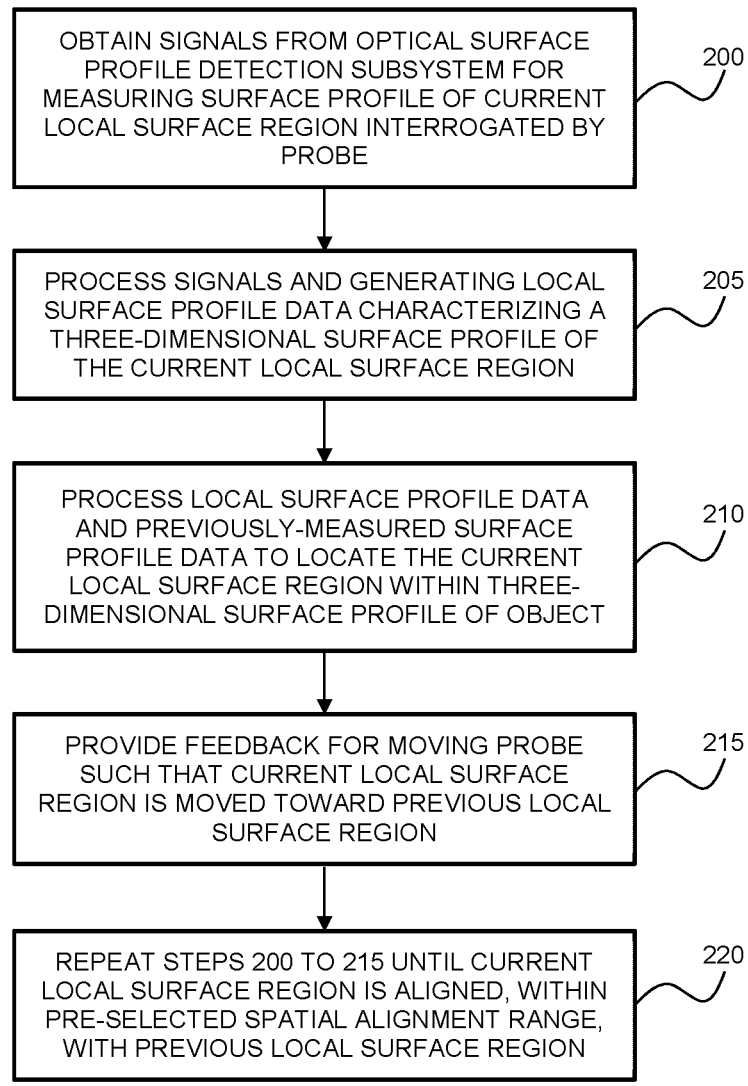
FIG. 4A is a flow chart illustrating an example method of providing feedback for positioning an integrated probe when repeating a diagnostic measurement, where the feedback is based on detection and processing of the surface profile.

As noted above, an integrated probe, such as the example integrated probes described in the embodiments shown above, may be beneficial in overcoming the aforementioned problems associated with diagnostic probe positioning, by providing feedback to assist in the positioning of the probe relative to the object being scanned. FIGS. 3A and 3B, and the flow chart provided in FIG. 4A, illustrate an example of such a method, in which feedback is provided for repeating a diagnostic measurement such that the probe is positioned to scan the same region that was previously scanned.

In FIG. 3A, the configuration of probe during the previous diagnostic measurement is shown relative to the dental arch, where the beam profile of the excitation beam 160 of the diagnostic detection subsystem is shown, along with the surface scanning beam 165 of the surface profile detection subsystem (it is noted that the phrase "excitation beam", as used herebelow, refers to the excitation beam of the diagnostic detection subsystem, and the phrase "surface scanning beam", as used herebelow, refers to the incident beam of the surface profile detection subsystem, which is employed to scan or otherwise measure the surface profile of the object). The surface profile detection subsystem is employed to detect and measure the surface profile of the local surface region 170 corresponding to the previous measurement.

The local surface region 170 corresponds to a portion of the extended surface region of the object under investigation. In the example shown in FIG. 3A, the local surface region overlaps three teeth, which is a subset of a dental arch. In several of the example embodiments described herein, surface profile information corresponding to an extended region of the object (e.g. global surface profile information) is also obtained, such that the extended surface region also includes the local surface region 170 of the previous diagnostic measurement (the previous local surface region). Accordingly, in the present example embodiment, the extended surface region, shown at 175, includes at least a portion of the dental arch. It is noted that the surface profile of the extended surface region 175 need not be measured using the integrated probe, and can be measured using any suitable imaging modality that is capable of providing surface profile data.

The recorded surface profile data from the previous local surface region 170 can then be compared to the surface profile data characterizing the surface profile of the extended surface region 175, such that the previous local surface region 170 can be located within the extended surface region 175. This comparison may be performed, for example, by employing any suitable image registration algorithm for performing image registration between the surface profile data characterizing the surface profile of the previous local surface region 170 and the surface profile data characterizing the surface profile of the extended surface region 175. An example of such an image registration algorithm is the iterative closed point (ICP) method. Other suitable image registration methods will be known to those skilled in the art.

FIG. 3B and FIG. 4A illustrate how guidance may be provided for positioning an integrated probe to repeat the diagnostic measurement such that the diagnostic detection subsystem scans the same region, or approximately the same region, of the object, based on the previously measured surface profile of the local surface region 170 and the extended surface region 175.

As shown in FIG. 3B, the integrated probe is incorrectly positioned too far to the left to properly repeat the diagnostic measurement previously made at local surface region 170. In order to determine the location of the current local surface region, the surface profile detection system of the integrated probe is employed to scan the current local surface region 170A with the surface scanning beam 165, as indicated in step 200 of FIG. 4A. The signals received by the surface profile detection subsystem are processed, as shown in step 205, to determine the three-dimensional surface profile of the current local surface region. This current local surface profile is then compared to the surface profile data characterizing the extended surface region 175, such that the current local surface region 170A can be located within the extended surface region 175, as shown in step 210. This comparison may be performed, for example, using an image registration algorithm such as the ICP method, or other suitable image registration methods, as noted above.

Having identified the location of the current local surface region 170A, its location relative to that of the previous local surface region 170 can be determined, and guidance is provided for moving the integrated probe relative to the object (or alternatively the object relative to the integrated probe) in order to bring the current local surface region closer to the previous local surface region, as shown at step 215. This process can be repeated until the current local surface region is deemed to be sufficiently close to the previous local surface region, as shown at step 220.

After sufficient correspondence of the current local surface region 170A to the previous local surface region 170 has been ascertained, feedback can be provided indicating that the integrated probe is now in a suitable location for repeating the previous diagnostic measurement.

The guidance is shown schematically in FIG. 3B by arrow 185, indicating the direction in which the integrated probe should be moved relative to the object in order to bring the current local surface region 170A closer to the previous local surface region 170. Although the figure shows an heuristic example in which the guidance is unidirectional, it will be understood that in general, the guidance may be provided in one, two or three directions.

It will be understood that the positional guidance can take on many possible forms. For example, the guidance could be in the form of a visible display showing the current probe position relative to the previous probe position, along with an indication, such as an arrow, of the direction in which the probe is to be moved, or via projection of an image onto the object being measured. The feedback may additionally or alternatively be provided acoustically, such as via the pitch of an audio signal, or via audible information regarding the direction in which the probe is to be moved. The feedback may also provide information regarding the relative proximity of the current local surface region 170A and the previous local surface region 170 (such as qualitative or quantitative proximity feedback provided on a visual display). In another example implementation, the positional guidance may take the form of control signals that are provided to a robotic positioning device supporting the integrated probe, such that the robotic positioning device can be controlled to automatically reposition the probe according to the control signals.

As noted above, the guidance may be provided regarding the positioning of the integrated probe until the current local surface region 170A sufficiently matches the previous local surface region 170. This sufficiency may be determined, for example, based on a pre-selected threshold associated with the completeness of the match between the current local surface region 170A and the previous local surface region 170. In one example implementation, the sufficiency criteria may merely require that the current local surface region 170A at least partially overlaps spatially with the previous local surface region 170. In other example implementations, a pre-selected overlap threshold may be specified, such that guidance is provided until the pre-selected overlap threshold is exceeded. Non-limiting examples for the overlap threshold include 5%, 10% overlap, 25% overlap, 50% overlap, 80% overlap, 90% overlap, 95% overlap, and 99% overlap. In another example implementation, the overlap threshold may be determined based on the spot size of the excitation energy beam of the diagnostic detection subsystem. It will be understood that the criterion or criteria for sufficiency of overlap between the current local surface region 170A and the previous local surface region 170 may depend on the application.

The positional guidance may be provided until the sufficiency over spatial overlap has been confirmed, and output may then be generated indicating that the integrated probe is in a suitable location for repeating the diagnostic measurement. In one example implementation, this output may be provided in the form of instructions or an alert to the operator. For example, the output may be provided as a visual indication on a user interface and/or an audio signal. In another example implementation, the output may automatically initiate the diagnostic measurement. This automation of the diagnostic measurement, based on the determination of sufficiency of spatial overlap, may be beneficial in further reducing operator error.

Figure 4B:
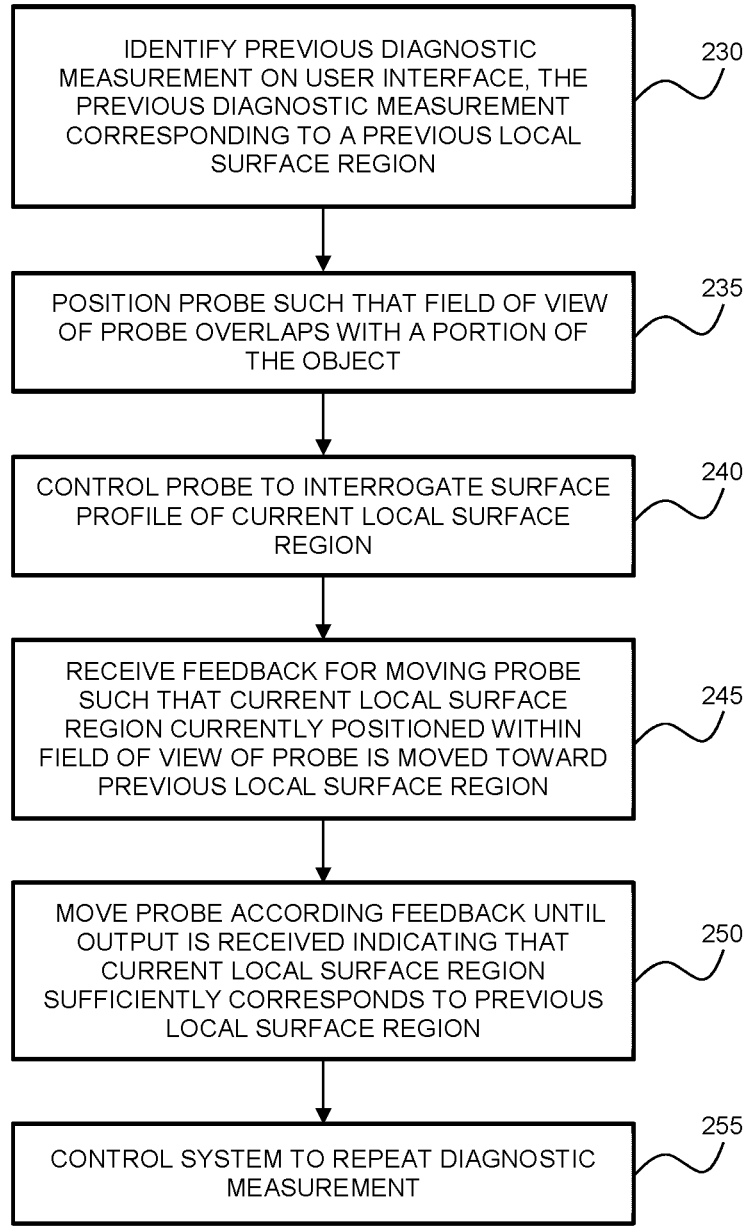
FIG. 4B is a flow chart illustrating an example method of positioning an integrated probe when repeating a diagnostic measurement in response to feedback based on detection and processing of the surface profile.

Referring now to FIG. 4B, a flow chart is provided that illustrates a method of employing an integrated probe to repeat a diagnostic measurement at a common location, the integrated probe having a diagnostic detection subsystem and a surface profile detection subsystem. In step 230, the operator identifies, on a user interface, a previous diagnostic measurement that is to be repeated. The system then obtains surface profile data stored in association with the previous diagnostic measurement, and previously measured surface profile data associated with the extended surface region. The operator then positions the probe such that the field of view of the probe is within the extended surface region (i.e. a portion of the object), as shown at step 235. The probe is then controlled, in step 240, to interrogate, with the surface profile detection subsystem, the surface profile of the current local surface region within the field of view of the probe. The local surface profile of the probe is then employed by the system to provide guidance feedback for positioning the probe such that the current local surface region is moved closer to the previous local surface region, as described above, and this feedback is received by the operator in step 245. As shown in step 250, the operator then moves the probe according to the feedback until output is received from the system indicating that the current local surface region sufficiently corresponds to the previous local surface region. The operator, receiving this output indicating correct spatial positioning of the probe, may then control the system to initial the repeating of the diagnostic measurement, as shown in step 255.

Figure 4C:
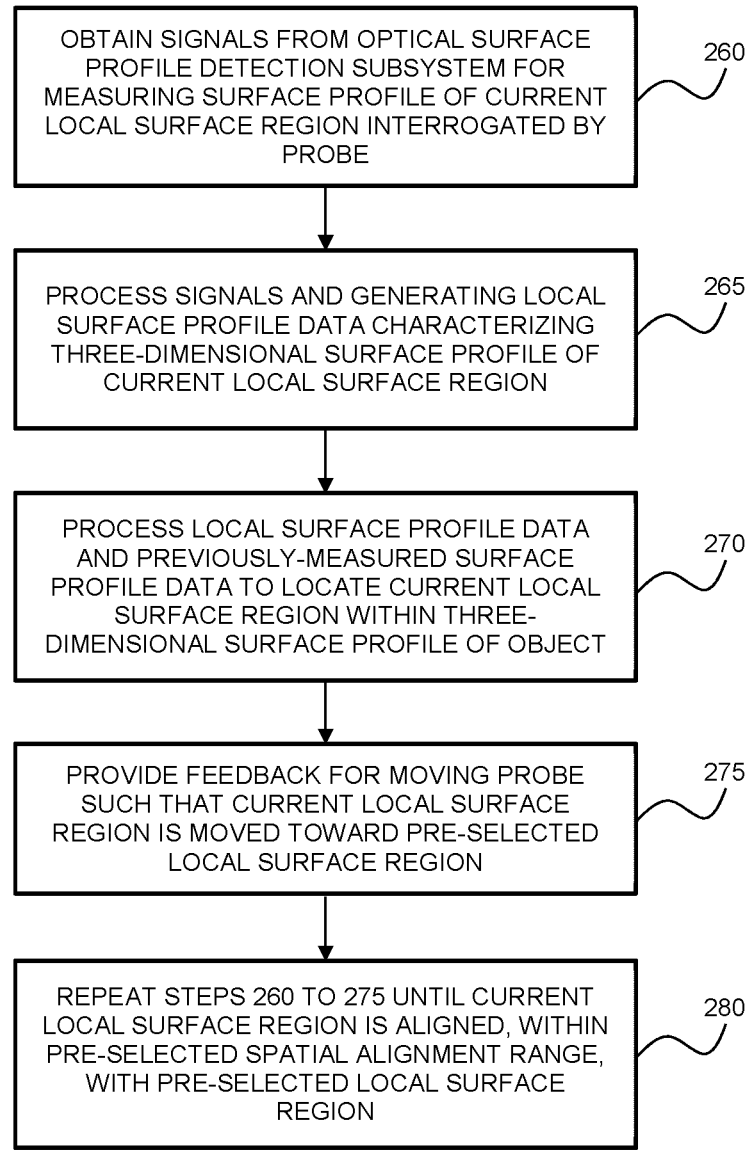
FIG. 4C is a flow chart illustrating an example method of providing feedback for positioning an integrated probe for positioning an integrated probe in a pre-selected position for performing a diagnostic measurement, where the feedback is based on detection and processing of the surface profile.

FIG. 4C illustrates an alternative example embodiment in which the surface profile detection subsystem is employed to provide guidance for positioning the integrated probe for performing a diagnostic measurement at or within a pre-selected local surface region. Steps 260 and 265 are employed to determine the surface profile of the current local surface region, as in steps 200 and 205 of FIG. 4A. This current local surface profile is compared to the surface profile data characterizing the extended surface region, such that the current local surface region can be located within the extended surface region, as shown in step 270. Having identified the location of the current local surface region, its location relative to that of the pre-selected local surface region can be determined, and guidance is provided for moving the integrated probe relative to the object (or alternatively the object relative to the integrated probe) in order to bring the current local surface region closer to the pre-selected local surface region, as shown at step 275. This process can be repeated until the current local surface region is deemed to be sufficiently close to the pre-selected local surface region, as shown at step 280.

Figure 5A:
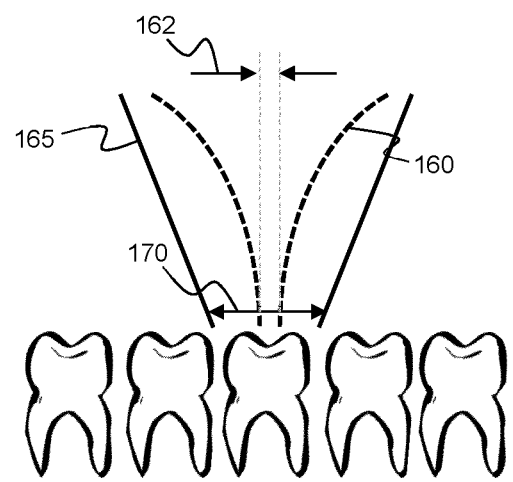
FIGS. 5A and 5B illustrate different example beam configurations of an integrated diagnostic probe.
Figure 5B:
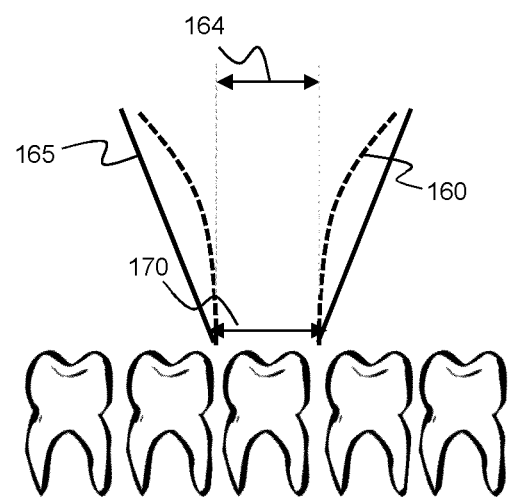

The example embodiments shown in FIGS. 2A, 2B, 3A and 3B, and 5A show the excitation beam 160 of the diagnostic detection subsystem focused to a small region relative to that of the surface scanning beam 165. For example, in FIG. 5A, the width of the surface region interrogated by the diagnostic detection subsystem is shown at 162 is more than 5 times less than that of the local surface region 170 that is interrogated by the surface scanning beam. In the alternative example embodiment shown in FIG. 5B, the size of the excitation beam 160 is approximately equal to that of the surface scanning beam 165. Such a configuration may be implemented in embodiments involving diagnostic detection subsystems that employ imaging as opposed to spot measurements. In other example implementations, the width of the excitation beam 160 may exceed that of the surface scanning beam 165.

In some example embodiments, the feedback is provided for controlling probe orientation (angulation), in addition to probe position. Maintaining probe orientation can be of importance in many cases due to the angular dependence of the detection process. This angular dependence of a diagnostic measurement may be due, for example, to angular changes in the reflectivity of a surface, especially in cases in which the excitation energy beam is polarized, and when the surface being interrogated is wet.

Figure 6:
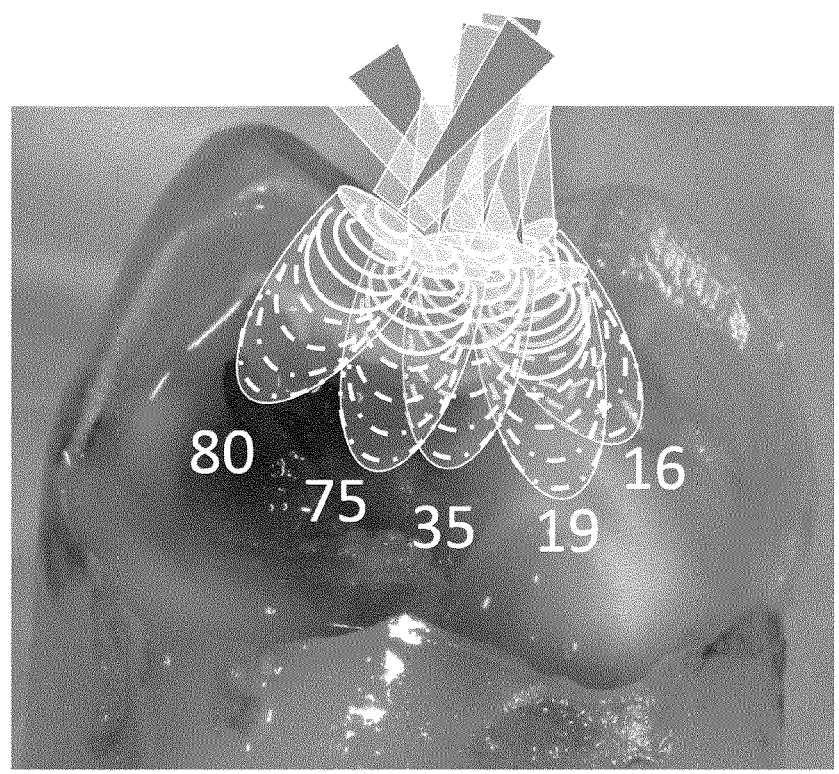
FIG. 6 shows the effect of varying the orientation of an integrated probe on the subsurface region that is interrogated by the probe, as illustrated in the example case of photothermal detection.
Figure 6:
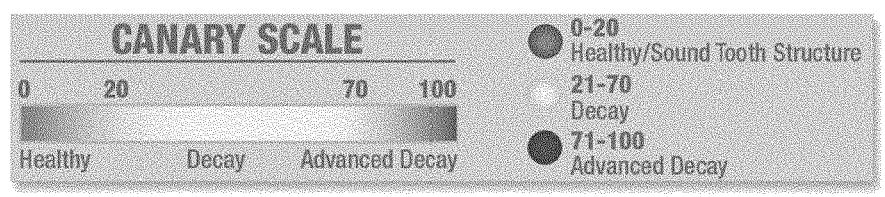

In some cases, the angular dependence of a diagnostic measurement made by a probe may arise from the depth-dependence of the measurement, as different angles will probe different surface regions and different depth regions. This effect is illustrated in FIG. 6, which shows the different spatial regions within a tooth that are probed when the angular orientation of a photothermal detection probe is varied. The angular dependence may result in large variations in signal strength (shown by the numbers overlaid on the figure), which is related to the density of the tooth structure below and the presence of decay. It therefore follows that if an operator wishes to repeat a previous diagnostic measurement of a particular region that previously resulted in a high signal (indicative of local tooth decay), then it will be important to repeat the diagnostic measurement with the probe in an orientation that corresponds to the previous probe orientation. It is noted that probe angulation can also impact measurements made with imaging modalities such as transillumination and fluorescence.

Accordingly, in some example embodiments, the comparison of the surface profile data obtained from the current local surface region (that is currently interrogated by a probe, when seeking to repeat a diagnostic measurement) is employed to determine the probe orientation relative to the extended spatial region, in addition to the location of the current local surface region within the extended spatial region. This example embodiment is illustrated in FIGS. 7A to 7C.

Figure 7A:
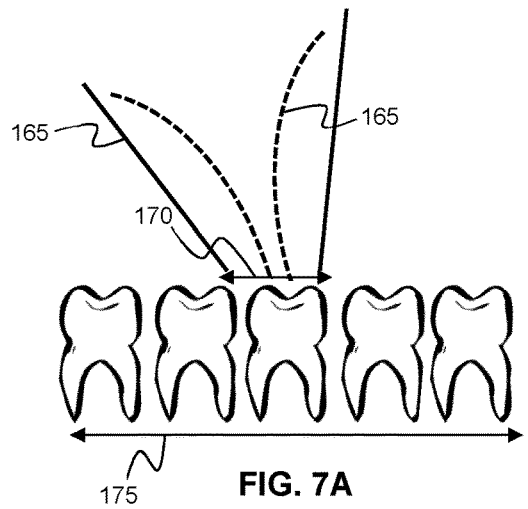
FIGS. 7A to 7C illustrate the re-orientation of an integrated probe according to guidance based on surface profile detection.

In FIG. 7A, the configuration of probe during the previous diagnostic measurement is shown relative to the dental arch, where the beam profile of the excitation beam 160 of the diagnostic detection subsystem is shown, along with the surface scanning beam 165 of the surface profile detections subsystem. In the present example, the previous probe orientation is angled relative to the dental arch. The surface profile detection subsystem is employed to detect and measure the surface profile of the local surface region 170 corresponding to the previous measurement.

The recorded surface profile data from the previous local surface region 170 can then be compared to the surface profile data characterizing the surface profile of the extended surface region 175 such that the previous local surface region 170 can be located within the extended surface region 175, as described above. In addition, a determination may also be made of the previous probe orientation by determining the viewing angle of the probe relative to the recorded surface, which can be established by spatially registering the surface profile data from the previous local surface region 170 to the surface profile data from the extended surface region 175.

Figure 7B:
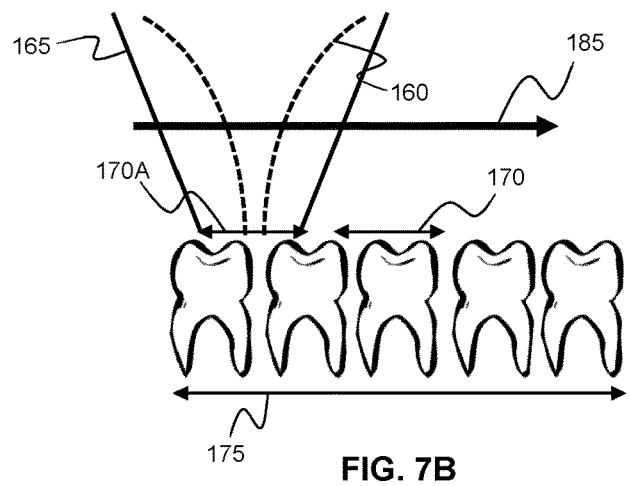
Figure 7C:
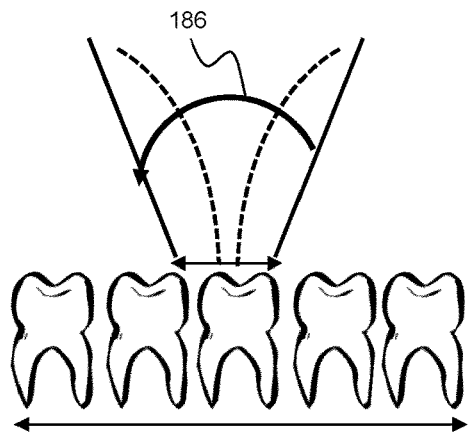

Referring now to FIGS. 7B and 7C, an example method is illustrated for providing guidance for positioning an integrated probe to repeat a diagnostic measurement such that the diagnostic detection subsystem scans the same region, or approximately the same region, of the object, at the same probe orientation, or approximately the same probe orientation, based on the previously measured surface profile of the local surface region 170 and the extended surface region 175.

As shown in FIG. 7B, the integrated probe is incorrectly positioned too far to the left, and in the incorrect probe orientation, to properly repeat the diagnostic measurement previously made at local surface region 170. In the present example method, guidance (shown schematically by arrow 185) is provided for moving the probe such that the current surface region 170A sufficiently corresponds to the previous local surface region, as describe in the preceding embodiments of the present disclosure (see, for example, FIGS. 3A, 3B and 4A).

The recorded surface profile data from the current local surface region 170A can then be compared to the surface profile data characterizing the surface profile of the extended surface region 175 in order to determine the current probe orientation by determining the viewing angle of the probe relative to the recorded surface, which can be established by the spatial registration of the surface profile data from the current local surface region 170A to the surface profile data from the extended surface region 175.

As shown in FIG. 7C, guidance then is provided for modifying the orientation of the probe such that the current probe orientation sufficiently corresponds to the orientation of the probe during the previous diagnostic measurement. The angular guidance is shown schematically in FIG. 7C by arrow 186, indicating the direction in which the integrated probe should be rotated relative to the object in order to bring the current probe orientation closer to the previous probe orientation.

It will be understood that the orientation guidance can take on many possible forms. For example, the guidance could be in the form of a visible display showing the current probe orientation relative to the previous probe orientation, along with an indication, such as an arrow, of the direction in which the probe is to be rotated. The feedback may additionally or alternatively be provided acoustically, such as via the pitch of an audio signal, or via audible information regarding the direction in which the probe is to be rotated. The feedback may also provide information regarding the relative error between the current probe orientation and the previous probe orientation (such as qualitative or quantitative proximity feedback provided on a visual display). In another example implementation, the orientation guidance may take the form of signals that are provided to a robotic positioning device supporting the integrated probe, such that the robotic positioning device can be controlled to automatically reorient the probe according to the control signals.

As noted above, the guidance may be provided regarding the orientation of the integrated probe until the current probe orientation sufficiently matches the previous probe orientation. This sufficiency may be determined, for example, based on a pre-selected threshold associated with the correspondence between the current probe orientation and the previous probe orientation. In one example implementation, the sufficiency criteria may be a permissible angular error interval. Non-limiting examples for the angular error interval include ±20°, ±10°, ±5°, ±2°, and ±1°. In another example implementation, the angular error interval may be determined based on the angular width of the excitation energy beam of the diagnostic detection subsystem. It will be understood that the criterion or criteria for sufficiency of the angular match between the current probe orientation and the previous probe orientation may depend on the application.

The positional and orientation guidance steps outlined above may be repeated, on an iterative basis, until sufficient positional and angular correspondence has been achieved for repeating the previous diagnostic measurement.

The aforementioned example embodiment regarding generating additional feedback for controlling the probe orientation may be also be implemented to supplement the example method described in FIG. 4C involving the use of feedback to position an integrated probe in a pre-selected position for performing a diagnostic measurement, such that feedback is also provided for orienting the probe in a pre-selected orientation for performing the diagnostic measurement.

The example embodiments described herein may be beneficial for improving and/or facilitating probe-based diagnostic measurements. Unlike known diagnostic devices that are only configured for performing diagnostic measurements, the present example embodiments involving the integration of a diagnostic detection subsystem with a surface profile detection subsystem enable more precise spatial and angular probe positioning by providing surface profile detection based guidance to an operator, or control signals to a robotic positioning system.

The use of such a system for performing repeated diagnostic measurements may be employed for the time-dependent tracking and monitoring regions of the object, such as regions of tissue that exhibit pathology or are suspected of exhibiting pathology (such as the examples provided herein involving the detection of oral heath pathology such as caries or demineralization), or regions associated with a therapeutic treatment. The repeated diagnostic measurements can be made in quick succession, such as within seconds or minutes, or over longer time intervals, such as hours, days, or years. The controlled re-positioning and/or reorientation of the probe, as enabled by the present example embodiments, may be useful in providing a more direct, "apples-to-apples" comparison between multiple measurements, by facilitating repeat measurements at a common location and/or orientation. For example, an initial measurement may be obtained as a baseline, and the use of surface profile detection as per the present example embodiments may be employed to provide repeated measurements.

The following example illustrates a non-limiting method involving the use of surface profilometry for repeating a probe-based diagnostic measurement with controlled probe position and/or angulation. In a first step, an integrated probe, capable of surface profile detection, and also capable of performing a diagnostic measurement on and/or below the surface of a tooth, performs surface or sub-surface measurement, while also performing local surface profile detection, and optionally capturing an image of the tooth.

The diagnostic measurement data may be processed to determine a status of the surface and sub-surface region in question. The associated image and diagnostic measurement data are stored. If the diagnostic measurement information includes sub-surface measurements including both depth and width of a lesion or area of pathology, then this information would be capture and saved. The data is stored with reference to a location on the dentition that is associated with the diagnostic measurement, and the diagnostic status information may be presented to an operator on an image or map showing this location.

At a later time, the diagnostic measurement may be repeated as follows. The integrated probe is moved back to the particular tooth surface, using the guidance method described above, based on the registration of surface profile topography data. When aligned with the correct location, a diagnostic measurement is again performed, and the diagnostic measurement data is captured and compared to the previously obtained diagnostic measurement data, in order to detect surface and/or subsurface changes. Information pertaining to the detected changes (e.g. changes in the oral health status of a tooth) is stored and may also be identified on a map or image of the tooth in question. If a series of measurements are taken over time, then a three-dimensional animation or image or series of images could be produced to show the changes in the area under examination. The animation would show, for example, the progression of the tooth decay, crack or re-hardening of the surface layers.

Figure 8:
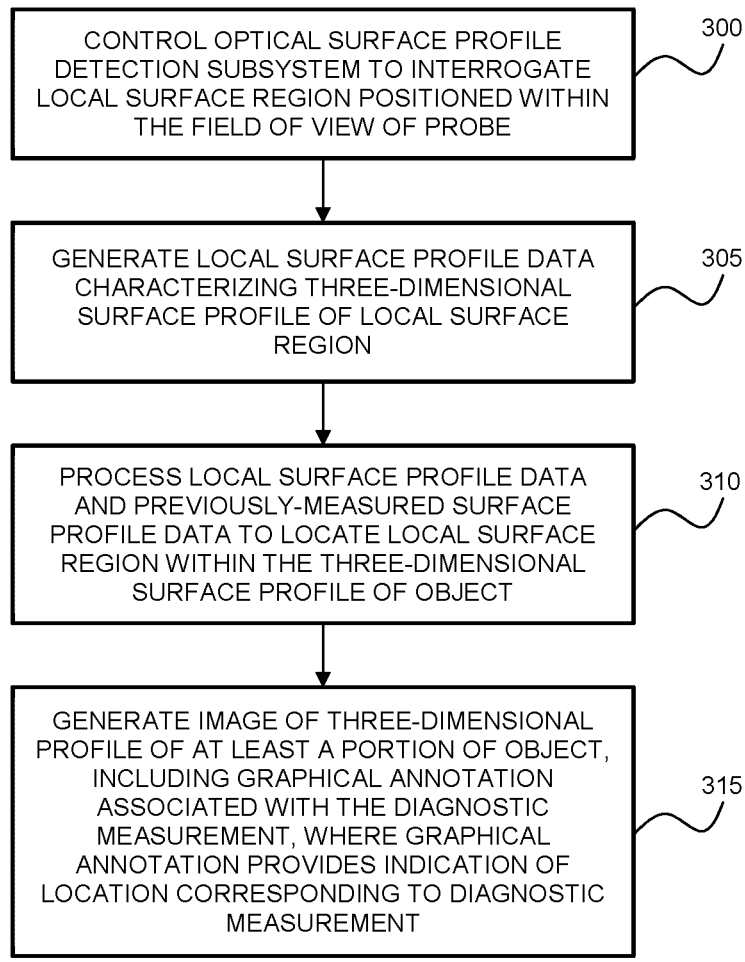
FIG. 8 is a flow chart illustrating an example method of inferring, based on surface profile detection, the position of an integrated probe when performing a diagnostic measurement, and annotating a three-dimensional image of an object such that the image is annotated to indicate the location of the diagnostic measurement.

In some example embodiments, the location of the local surface region interrogated by the integrated probe, and optionally the probe orientation, as determined by comparing the surface profile data from the local surface region to the surface profile data from the extended region, may be employed to annotate a visual display. An example of such an embodiment is illustrated in the flow chart provided in FIG. 8. In step 300, the surface profile detection subsystem is employed to interrogate the surface profile of the local surface region. The signals received by the surface profile detection subsystem are then employed, in step 305, to generate surface profile data characterizing the surface profile of the local surface region. In step 310, this surface profile data is then compared to surface profile data characterizing the surface profile of the extended surface region (a surface region of at least a portion of the object being interrogated, such that the extended surface region includes the local surface region), in order to locate the surface region within the surface profile of the extended region, as described in the preceding embodiments (e.g. via image registration methods). The comparison may also optionally be employed to determine the probe orientation, as explained above. The location and optional orientation information may then be employed to annotate a three-dimensional image of the extended surface region of the object (or at least a portion thereof), showing, for example, the current local surface region being interrogated, and/or the current probe orientation. When a diagnostic measurement is made with the integrated probe, the annotation may show at least one or more of: the local surface region corresponding to the diagnostic measurement, the probe orientation corresponding to the diagnostic measurement, results from the diagnostic measurement, and an oral health status measure obtained by processing, at least in part, the diagnostic measurement, and time-dependent measures associated repeated diagnostic measurements. Examples of such annotations are provided in the forthcoming examples section.

In one example embodiment, surface profile detection may be employed to measure changes in surface topography, such as changes in surface tissue, loss of surface integrity or loss of surface tissue. For example, if two repeated measurements of the surface profile of a region of interest (which may include any portion or all of the dentition) are obtained, a spatially registered there among, then changes in the surface topography may be determined by subtraction. The change in surface topography may be employed to identify, for example, regions associated with erosion of a tooth surface and/or regions associated with a loss of tissue.

In one example embodiment, an integrated diagnostic probe may be provided with both a therapeutic tissue removal device and a diagnostic measurement device. Examples of therapeutic devices include, for example, a cutting instrument, such as a rotary bur and or a therapeutic laser suitable for performing ablation. In a first step, a location associated with a pathology is determined by performing diagnostic measurements with the integrated probe. For example, diagnostic data obtained by the probe may be compared with reference values associated with healthy tissue in order to identify an area of pathology.

The location associated with the pathology may have been identified at a previous point in time, and provided that the integrated probe includes a surface profile detection device, the aforementioned surface profile based guidance method may be employed to reposition (and optionally reorient) the probe at the location associated with the pathology.

Having located the integrated probe at the location associated with the detected pathology, the cutting instrument is employed to remove a first layer of tissue. After removal of the initial layer of tissue, the diagnostic measurement is again performed, in order to determine whether or not a sufficient amount of tissue has been removed in order to correct the pathology. If the presence of the pathology is still detected, the cutting instrument is again employed to remove a subsequent layer. It is noted that in some cases, there it may be necessary cut through one or more layers of healthy tissue if the diagnostic measurement associated with the pathology originated from subsurface layers. For example, tooth decay may sometimes be covered by healthy enamel, but the photothermal signals may indicate that there is decay present due to decay in layers beneath the enamel. In another example decay may be on the side or interproximal contact area of the tooth beneath the contact point or area which contacts with the adjacent tooth. Gaining access to the decayed region would involve cutting through healthy tooth structure. This iterative process of diagnostic measurement and subsequent tissue removal may be repeated until the pathology is no longer detected.

The aforementioned surface-profile-based guidance method may be employed prior to repeating the diagnostic measurement and/or repeating the cutting step, in order to ensure the correct position (and optionally, the correct orientation) of the probe at each step. For example, an initial local surface profile obtained when performing the initial diagnostic measurement (identifying the pathology) may be compared to a current local surface profile that is detected prior to performing a subsequent diagnostic measurement or therapeutic tissue removal step, and the initial local surface profile and the current local surface profile may be processed to identify the presence of a positional and/or orientational misalignment. Further diagnostic measurements and/or tissue removal steps may be prohibited until the misalignment is corrected. The system may provide guidance information to the operator in order to correct a misalignment, as described above.

In one example implementation, at least some of the steps in the method described above may be automated, such that, provided that the probe position (and optionally, the probe orientation) is maintained (i.e. matches the initial probe position/orientation within a prescribed tolerance range), the integrated device is controlled to automatically proceed with additional diagnostic measurements and/or cutting steps when the presence of the pathology is detected.

In some example embodiments, the repeating of the cutting steps may be initiated (e.g. or authorized) via an operator, such that the operator has the ability to review the most recent diagnostic measurement before continuing with the removal of tissue.

In another example embodiment, a diagnostic probe may be employed to detect alveolar bone height around a tooth via infrared detection, which is known to be impacted by the progression of gingivitis, as shown in FIGS. 13A-C. In one example embodiment, the integrated probe is equipped with a surface profile detection subsystem and an infrared diagnostic subsystem, where the infrared diagnostic subsystem is configured to direct an infrared beam onto a gingival surface, and to detect, via changes in the intensity of the scattered infrared light, the presence of alveolar bone beneath gingival tissue. According to the present example embodiment, the surface profile detection subsystem is employed to detect a surface profile of the gum and tooth surface on the outer (buccal) and inner (lingual/palatal) aspects of the maxilla and or mandible, thereby spatially referencing measurements made by the infrared detection system to the three-dimensional surface profile. As the integrated probe is moved across these surfaces, the resulting surface profile data could be employed to confirm or provide feedback relating to a desired orientation and/or position of the probe. The infrared detection system scans an infrared beam (or obtains an infrared image) across at least a portion of the gum surface, and the scattered infrared light is processed to identify the top of the underlying supporting or alveolar bone. The height or position of the bone with respect to the top or crest of the overlying gum tissue could be determined based on the spatial registration of the locations of the infrared measurements with the three-dimensional surface profile. The height or position of the top of the tooth associated with the gum tissue, as determined based on the three-dimensional surface data, may also be employed as a reference location. In another example implementation, the bone height could be measured or determined by comparing the height of bone (measured as described above) to the tip of the gum or gingival tissue collar that surrounds a tooth, which is currently measured using a hand held probe which is placed into a gum pocket at various positions around the tooth surface.

The scan or examination of height of the alveolar bone would be recorded and optionally plotted, and this information could be compared to examinations performed at a later date. In one example embodiment, the position of the bone is shown on an image that shows the tooth surface, the gum tissue (e.g. an image generated based on the recorded surface profile) and optionally the bone beneath the gum tissue, for example, as shown in FIGS. 13D and 13E.

Figure 9:
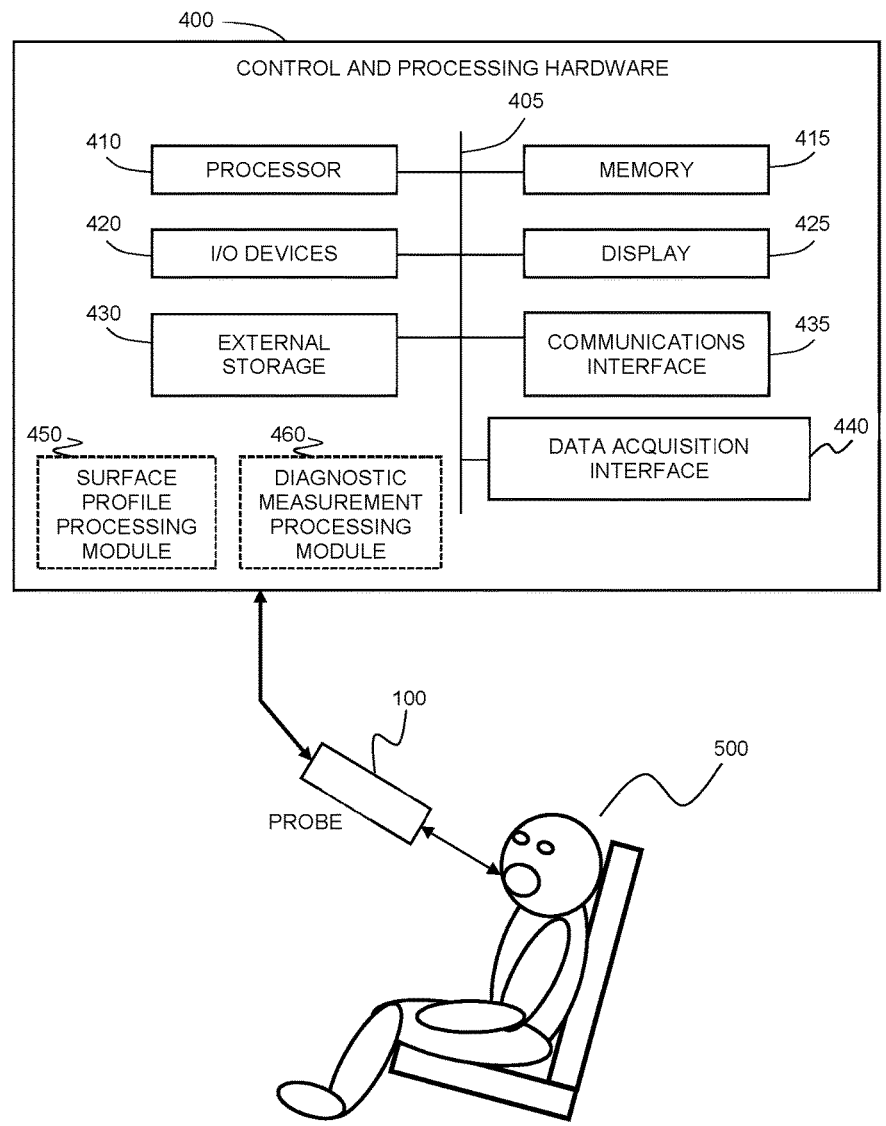
FIG. 9 shows an example system for providing guidance for positioning, and optionally orienting, an integrated probe based on surface profile detection.

Referring now to FIG. 9, an example system is shown for providing feedback for guidance to position an integrated probe, and to optionally orient the integrated probe, for performing diagnostic measurements. The example system includes an integrated probe 100 that is operatively coupled to a control and processing unit 400. Integrated probe 100 may be based, for example, on the example integrated probe embodiments shown in FIGS. 2A-2D, or alternative probe embodiments such as those described above. During use, the integrated probe 100 may be placed in close proximity to the subject 500 for performing a diagnostic measurement on an object, such as a portion of an anatomical region, which may be an internal or external portion of the subject's anatomy, including hard and/or soft tissues. In the example system shown in FIG. 9, the integrated probe is an intraoral probe.

As shown in the example embodiment illustrated in FIG. 9, control and processing hardware 400 may include a processor 410, a memory 415, a system bus 405, one or more input/output devices 420, and a plurality of optional additional devices such as communications interface 435, display 425, external storage 430, and data acquisition interface 440.

The present example methods for performing guidance based on surface profile detection can be implemented via processor 410 and/or memory 415. As shown in FIG. 9, the processing of signals received by the surface profile detection subsystem of the probe 100 is performed by control and processing hardware 400, via executable instructions represented as surface profile processing module 450. The control and processing hardware 400 may include and execute instructions for processing diagnostic measurements made by the diagnostic detection subsystem of probe 100, for example, in order to calculate risk or diagnosis measures, as represented by diagnostic measurement processing module 460.

The methods described herein can be partially implemented via hardware logic in processor 410 and partially using the instructions stored in memory 415. Some embodiments may be implemented using processor 410 without additional instructions stored in memory 415. Some embodiments are implemented using the instructions stored in memory 415 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 400 may be provided as an external component that is interfaced to a processing device. For example, one or more components of the control and processing hardware 400 may be provided within probe 100.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

It will be understood that the example integrated probe embodiments disclosed herein may be employed for performing probe-based diagnostic measurements of a wide range of tissue types. In some embodiments, the probe is configured to perform diagnostic measurements of tissues other than hard tissue. For example, the probe may also be configured for performing measurements, with the diagnostic detection subsystem, of soft tissues, in parallel with the detection of the surface profile of the soft tissue (optionally also including hard tissue surfaces). The example integrated probe embodiments disclosed herein may also or alternatively be employed for non-medical purposes, for the detection of signals, in conjunction with surface profile measurements, from a wide range of different objects. For example, in one example implementation, an integrated probe according to any of the embodiments disclosed herein or variants thereof, having both diagnostic measurement and surface profile detection capabilities, may be employed in robotic assembly lines, for example, for performing quality control.

EXAMPLES

The following examples are presented to enable those skilled in the art to understand and to practice embodiments of the present disclosure. They should not be considered as a limitation on the scope of the disclosure, but merely as being illustrative and representative thereof.

Figure 10A:
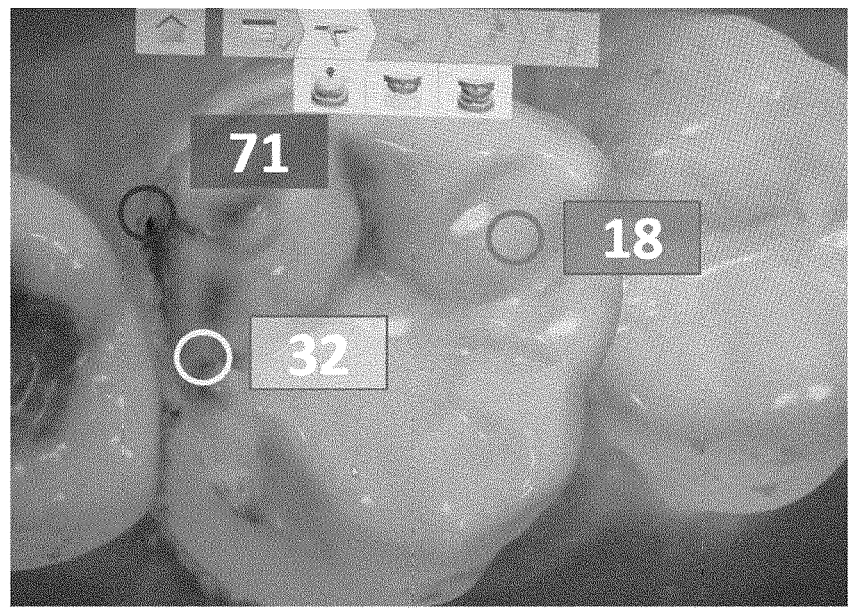
FIGS. 10A and 10B show example images of teeth annotated with metadata associated with a plurality of diagnostic measurements made with an integrated probe.
Figure 10B:
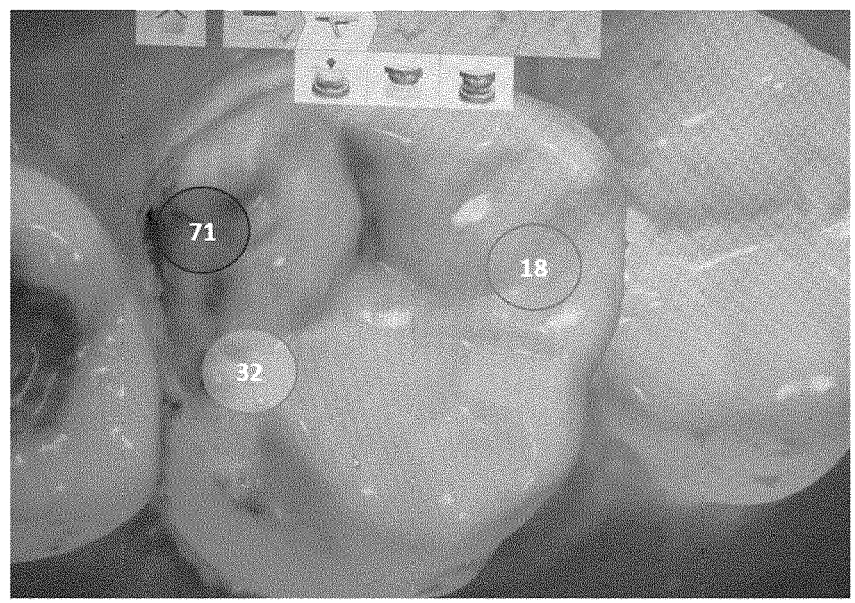

Example 1: Digital Dental Surface Profile Images Overlaid with Diagnostic Detection Values FIGS. 10A and 10B show two example 3D images, generated using the optical scanning of tooth surfaces, where the images overlaid with diagnostic detection values ("Canary Numbers") obtained via the processing of photothermal and luminescence measurements. The diagnostic detection values are shown at their corresponding measurement locations.

Figure 11:
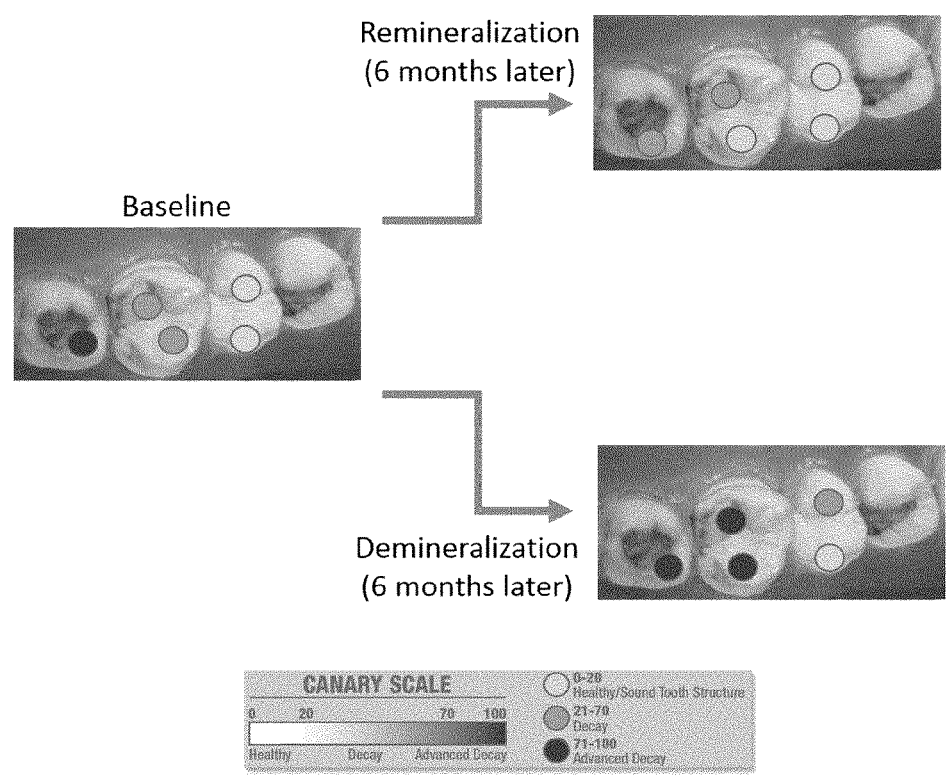
FIG. 11 shows example images of teeth with annotations indicating the location of diagnostic measurements, and qualitative measures of local decay according to the diagnostic measurements, illustrating how repeat local measurements performed according to the present example embodiments enable the tracking of changes in local oral health status.

FIG. 11 illustrates how the spatial mapping of results obtained from the diagnostic detection subsystem can be overlaid on top of 3D images obtained from the surface profile detection subsystem, showing the location of quantification of the health state of a given surface region. The present example illustrates how the diagnostic detection values (Canary Numbers) can change between baseline values and values detected at a later time period (e.g. 6 months), enabling the detection of remineralization or demineralization of the same local region on a given local surface.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A system for performing a probe-based diagnostic measurement, the system comprising:
   a probe comprising:
   an optical surface profile detection subsystem configured to direct optical energy onto a local surface region of an object and to detect, from the local surface region, scattered optical energy suitable for generating a surface profile of the local surface region; and
   a diagnostic subsystem aligned relative to said optical surface profile detection subsystem, wherein said diagnostic subsystem is configured to interrogate the local surface region and/or a subsurface region beneath the local surface region; and
   control and processing hardware operatively coupled to said optical surface profile detection subsystem and said diagnostic subsystem;
   wherein said control and processing hardware is configured to perform the following operations to provide guidance for positioning said probe to repeat a previous diagnostic measurement, wherein the previous diagnostic measurement was performed at a previous local surface region:
   a) controlling said optical surface profile detection subsystem to interrogate a current local surface region that is currently within a field of view of said optical surface profile detection subsystem, and obtaining signals from said optical surface profile detection subsystem that are generated in response to detection of the scattered optical energy;
   b) processing the signals and generating local surface profile data characterizing a three-dimensional surface profile of the current local surface region;
   c) processing the local surface profile data and previously-measured surface profile data to locate the current local surface region within the three-dimensional surface profile of the object, the previously-measured surface profile data characterizing a three-dimensional surface profile of at least a portion of the object;
   d) providing feedback for moving said probe such that the current local surface region is moved toward the previous local surface region;
   e) repeating steps a) to d) until the current local surface region is aligned, within a pre-selected spatial alignment range, with the previous local surface region; and
   f) providing output suitable to initiate the repeating of the diagnostic measurement.

2. The system according to claim 1 wherein said output is employed to automate the repeating of the diagnostic measurement, such that the repeat diagnostic measurement is automatically performed once the current local surface region is aligned, within the pre-selected spatial alignment range, with the previous local surface region.

3. The system according to claim 1 wherein the previous diagnostic measurement was performed with said probe oriented in a previous probe orientation, and wherein said control and processing hardware is further configured to perform operations to provide guidance for orienting said probe such that:
   step c) further comprises processing the local surface profile data and the previously-measured surface profile data to determine a current probe orientation of said probe relative to the object;
   step d) further comprises providing feedback for orienting said probe such that the current probe orientation is angled toward the previous probe orientation; and
   step e) further comprises repeating steps a) to d) until the current probe orientation is aligned, within a pre-selected angular alignment range, with the previous probe orientation.

4. The system according to claim 3 wherein said output is employed to automate the repeating of the diagnostic measurement, such that the repeat diagnostic measurement is automatically performed once the current local surface region is aligned, within the pre-selected spatial alignment range, with the previous local surface region, and said probe is aligned, within the pre-selected angular alignment range, with the previous probe orientation.

5. The system according to claim 1 further comprising repeating steps a) to f) one or more times to obtain a plurality of diagnostic measurements, wherein said control and processing hardware is further configured to process the plurality of diagnostic measurements to determine one or more time-dependent measures associated with one or more of the local surface region and the subsurface region beneath the local surface region.

6. The system according to claim 1 wherein said optical surface profile detection subsystem comprises:
   an optical projection source configured to project, from a distal region of said probe, one or more structured light patterns onto the surface; and
   an imaging detector configured to detect scattered optical radiation having surface profile information encoded therein.

7. The system according to claim 1 wherein said diagnostic subsystem employs an optical diagnostic modality, and wherein said diagnostic subsystem and said optical surface profile detection subsystem share at least one optical component.

8. The system according to claim 1 wherein said diagnostic subsystem comprises an ultrasound transducer for performing ultrasound diagnostic measurements.

9. The system according to claim 1 wherein said diagnostic subsystem is configured to direct a laser beam onto the local surface region, and wherein the laser beam is suitable for generating photothermal radiation with the subsurface region, and wherein said diagnostic subsystem further comprises collection optics and a mid-infrared detector, wherein said mid-infrared detector is configured for detecting the photothermal radiation.

10. The system according to claim 9 wherein said diagnostic subsystem further comprises an additional detector configured for detection of luminescence radiation emitted at the local surface region or within the subsurface region in response to absorption of the laser beam.

11. The system according to claim 1 wherein at least a portion of said control and processing hardware is housed within said probe.

12. The system according to claim 1 wherein said control and processing hardware is further configured to generate a surface image of the three-dimensional profile of at least a portion of the object, the surface image comprising a graphical annotation associated with one or more of the previous diagnostic measurement and the repeated diagnostic measurement, wherein the graphical annotation provides an indication of the location corresponding to one or more of the previous diagnostic measurement and the repeated diagnostic measurement.

13. The system according to claim 1 wherein said probe is an intraoral diagnostic probe, such that said diagnostic subsystem is configured for performing oral diagnostic measurements; and
wherein the object is a dental arch, including one or both of hard and soft tissues, such that the previously-measured surface profile data characterizes the surface area of at least a portion of the dental arch.

14. The system according to claim 1 wherein said diagnostic subsystem comprises an imaging device configured to obtain an image of the object, the image including at least the local surface region, and wherein the diagnostic measurement comprises obtaining the image with said imaging device.

15. The system according to claim 14 wherein said imaging device is selected from the group comprising a high-definition colour camera, an infrared imaging camera, and an ultrasound imaging device.

16. A method of repeating a previous diagnostic measurement with the system according to claim 1, the method comprising:
identifying the previous diagnostic measurement on a user interface operably interfaced with the system, and wherein the previous diagnostic measurement has associated therewith the previous local surface region;
positioning the probe such that the field of view of the probe overlaps with a portion of the object to be re-measured;
controlling the probe to interrogate the surface profile of the current local surface region;
receiving the feedback from the system for moving the probe such that the current local surface region currently positioned within the field of view of the probe is moved toward the previous local surface region;
moving the probe according the feedback until output is received indicating that the current local surface region sufficiently corresponds to the previous local surface region; and
controlling the system to repeat the diagnostic measurement.

17. The method according to claim 16 wherein the previous diagnostic measurement was performed with said probe oriented in a previous probe orientation, and wherein said control and processing hardware is further configured to perform operations to provide guidance for orienting said probe such that:
step c) further comprises processing the local surface profile data and the previously-measured surface profile data to determine a current probe orientation of said probe relative to the object;
step d) further comprises providing feedback for orienting said probe such that the current probe orientation is angled toward the previous probe orientation; and
step e) further comprises repeating steps a) to e) until the current probe orientation is aligned, within a preselected angular alignment range, with the previous probe orientation; and
wherein the previous diagnostic measurement has associated therewith the previous probe orientation;
wherein the feedback received from the system is further provided for orienting the probe such that the current probe orientation is angled toward the previous probe orientation; and
wherein moving the probe further comprises orienting the probe according the feedback until output is received indicating that the current probe orientation sufficiently corresponds to the previous probe orientation.

18. The method according to claim 16 wherein the probe is an intraoral diagnostic probe, such that the diagnostic subsystem is configured for performing dental diagnostic measurements; and
wherein the object is a dental arch, including one or both of hard and soft tissues, such that the previously-measured surface profile data characterizes the surface area of at least a portion of the dental arch; and
wherein the diagnostic subsystem is configured to detect energy signals generated beneath the surface of a tooth.

19. A system for performing a probe-based diagnostic measurement, the system comprising:
a probe comprising:
an optical surface profile detection subsystem configured to direct optical energy onto a local surface region of an object and to detect, from the local surface region, scattered optical energy suitable for generating a surface profile of the local surface region; and
a diagnostic subsystem aligned relative to said optical surface profile detection subsystem, wherein said diagnostic subsystem is configured to interrogate the local surface region and/or a subsurface region beneath the local surface region; and
control and processing hardware operatively coupled to said optical surface profile detection subsystem and said diagnostic subsystem;
wherein said control and processing hardware is configured to perform the following operations in association with a diagnostic measurement made at the local surface region:
a) controlling said optical surface profile detection subsystem to interrogate the local surface region positioned within the field of view of said probe, and obtaining signals from said optical surface profile detection subsystem that are generated in response to detection of the scattered optical energy;
b) processing the signals and generating local surface profile data characterizing a three-dimensional surface profile of the local surface region;
c) processing the local surface profile data and previously-measured surface profile data to locate the local surface region within the three-dimensional surface profile of the object, the previously-measured surface profile data characterizing a three-dimensional surface profile of at least a portion of the object; and
d) generating an image of the three-dimensional profile of at least a portion of the object, the image comprising a graphical annotation associated with the diagnostic measurement, wherein the graphical annotation provides an indication of the location corresponding to the diagnostic measurement.

20. A method of controlling a diagnostic and therapeutic probe, the diagnostic and therapeutic probe comprising:
an optical surface profile detection subsystem configured to direct optical energy onto a local surface region of an object and to detect, from the local surface region, scattered optical energy suitable for generating a surface profile of the local surface region;
a diagnostic subsystem aligned relative to the optical surface profile detection subsystem, wherein the diagnostic subsystem is configured to interrogate the local surface region and/or a subsurface region beneath the local surface region; and a therapeutic subsystem aligned relative to the optical surface profile detection subsystem, wherein the therapeutic subsystem is configured for local tissue removal;

the method comprising:
- a) employing the diagnostic and therapeutic probe to identify an initial surface region associated with a surface or subsurface pathology;
- b) employing the optical surface profile detection subsystem to interrogate the initial surface region, and obtaining signals from the optical surface profile detection subsystem that are generated in response to detection of optical energy scattered from the initial surface region;
- c) processing the signals and generating initial local surface profile data characterizing a three-dimensional surface profile of the initial surface region;
- d) sending control signals to the therapeutic subsystem to initiate removal of a first tissue layer;
- e) performing an additional diagnostic measurement with the diagnostic subsystem to determine whether or the pathology is still present;
- f) in the event that the presence of the pathology is detected, sending control signals to the therapeutic subsystem to initiate removal of an additional layer of tissue; and
- g) repeating steps e) and f) until the pathology is no longer detected;

wherein prior to performing one or both of steps e) and f), the following steps are performed to ensure correct positional and/or orientational alignment of the diagnostic and therapeutic probe:

employing the optical surface profile detection subsystem to interrogate a current local surface region that is currently within a field of view of the optical surface profile detection subsystem, and obtaining additional signals from the optical surface profile detection subsystem that are generated in response to detection of optical energy scattered from the current local surface region;

processing the additional signals and generating current local surface profile data characterizing a three-dimensional surface profile of the current local surface region;

processing the initial local surface profile data and the current local surface profile data to identify a positional and/or orientational misalignment of the diagnostic and therapeutic probe relative to an initial position and orientation of the diagnostic and therapeutic probe when the local surface region was identified in step a); and in the event of detection of the positional and/or orientational misalignment of the diagnostic and therapeutic probe, preventing further diagnostic measurements or tissue removal steps until the positional and/or orientational misalignment is corrected.

21. A method of measuring alveolar bone height using a diagnostic probe, the diagnostic probe comprising:

an optical surface profile detection subsystem; and an infrared detection subsystem aligned relative to the optical surface profile detection subsystem, wherein the infrared detection subsystem is configured direct infrared light onto a tissue surface and detect scattered infrared light from tissue regions below the tissue surface;

the method comprising:
while moving the diagnostic probe relative at least a portion of the maxialla and mandible;
employing the optical surface profile detection subsystem to direct optical energy onto a plurality of tooth and gum surfaces, and to detect, spatial profile signals associated with scattered optical energy;
employing the infrared detection subsystem to direct infrared light onto the gum surfaces, and detecting infrared signals associated with scattered infrared light that is scattered from regions below the gum surfaces;
processing the spatial profile signals to determine a three-dimensional surface profile associated with the plurality of tooth and gum surfaces;
processing the infrared signals and the surface profile to identify alveolar bone regions within the surface profile that are associated with the presence of alveolar bone beneath the tissue surface.

22. The method according to claim 21 further determining an upper margin associated with each of the alveolar bone regions.

23. The method according to claim 22 further comprising generating an image showing the upper margin relative to the surface profile.

24. The method according to claim 22 further processing the surface profile to determine one or more reference locations associated with each tooth scanned by the diagnostic probe, and comparing the reference locations to the upper margin in order to determine a spatial profile of the height of the alveolar bone.

* * * * *